United States Patent [19]

Chan et al.

[11] 4,321,209
[45] Mar. 23, 1982

[54] FLUORINATED AROMATIC POLYENES

[75] Inventors: Ka-Kong Chan, Hopatcong; Beverly A. Pawson, Montclair, both of N.J.

[73] Assignee: Hoffmann-La Roche Inc., Nutley, N.J.

[21] Appl. No.: 206,197

[22] Filed: Nov. 12, 1980

Related U.S. Application Data

[60] Division of Ser. No. 96,362, Nov. 21, 1979, which is a division of Ser. No. 37,798, May 10, 1979, Pat. No. 4,201,727, which is a division of Ser. No. 952,416, Oct. 18, 1978, Pat. No. 4,169,100, which is a division of Ser. No. 809,738, Jun. 24, 1977, Pat. No. 4,137,246, which is a continuation-in-part of Ser. No. 722,939, Sep. 13, 1976, abandoned, which is a continuation-in-part of Ser. No. 632,028, Nov. 14, 1975, abandoned.

[51] Int. Cl.³ .............................................. C07C 63/52
[52] U.S. Cl. .................................................. 260/408
[58] Field of Search ........................................ 260/408

[56] References Cited

U.S. PATENT DOCUMENTS

| | | | |
|---|---|---|---|
| 3,163,669 | 12/1964 | Stilz | 260/408 |
| 3,657,306 | 4/1972 | Murray | 260/408 |
| 3,862,969 | 1/1975 | Henrick | 260/408 |
| 3,954,817 | 5/1976 | Jager | 260/408 |

FOREIGN PATENT DOCUMENTS

| | | |
|---|---|---|
| 2414619 | 10/1974 | Fed. Rep. of Germany . |
| 2542612 | 4/1976 | Fed. Rep. of Germany . |
| 1079217 | 8/1967 | United Kingdom . |
| 1442108 | 7/1976 | United Kingdom . |
| 1468401 | 3/1977 | United Kingdom . |

OTHER PUBLICATIONS

Bollag et al., Chem. Abst. 82:111778x, (1975).
Ike et al., Bull. Chem. Soc., Jap., vol. 47, pp. 350-354, (1974).

*Primary Examiner*—John F. Niebling
*Attorney, Agent, or Firm*—Jon S. Saxe; Bernard S. Leon; George W. Johnston

[57] ABSTRACT

Compounds represented by the formula

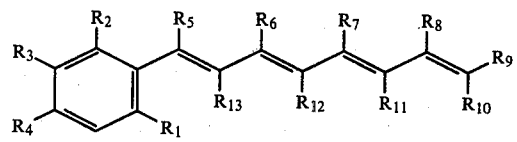

wherein $R_1$, $R_2$ and $R_3$ are lower alkyl, $R_4$ is lower alkoxy, $R_6$ and $R_8$ are methyl or trifluoro methyl, $R_9$ is formyl, hydroxymethyl, alkoxymethyl, alkanoyloxymethyl, carboxyl, alkoxycarbonyl, lower alkenoxycarbonyl, lower alkynoxycarbonyl, carbamoyl, mono(-lower alkyl)-carbamoyl, di(lower alkyl)carbamoyl or N-heterocyclylcarbonyl, $R_5$, $R_7$, $R_{10}$, $R_{11}$, $R_{12}$ and $R_{13}$ are hydrogen or fluorine with the proviso that at least one of $R_5$, $R_7$, $R_{10}$, $R_{11}$, $R_{12}$ or $R_{13}$ is fluorine or at least one of $R_6$ or $R_8$ is trifluoro methyl, or pharmaceutically acceptable salts thereof useful as antitumor agents are disclosed.

2 Claims, No Drawings

FLUORINATED AROMATIC POLYENES

RELATED APPLICATIONS

This is a division, of application Ser. No. 96,362 filed Nov. 21, 1979 which in turn is a division of Ser. No. 37,798, filed May 10, 1979, now U.S. Pat. No. 4,201,727, which in turn is a division of Ser. No. 952,416, filed Oct. 18, 1978, now U.S. Pat. No. 4,169,100, which in turn is a division of Ser. No. 809,738, filed June 24, 1977, now U.S. Pat. No. 4,137,246, which in turn is a continuation-in-part of Ser. No. 722,939, filed Sept. 13, 1976, now abandoned, which in turn is a continuation-in-part of Ser. No. 632,028, filed Nov. 14, 1975, now abandoned.

DESCRIPTION OF THE INVENTION

The present invention relates to polyene compounds. More particularly, the invention is concerned with fluorinated aromatic polyene compounds, a process for the manufacture thereof and pharmaceutical preparations containing same.

The polyene compounds provided by the present invention are represented by the following formula

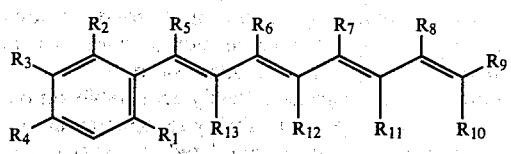

I wherein $R_1$, $R_2$ and $R_3$ are lower alkyl, $R_4$ is lower alkoxy, $R_6$ and $R_8$ are methyl or trifluoromethyl, $R_9$ is formyl, hydroxymethyl, alkoxymethyl, alkanoyloxymethyl, carboxyl, alkoxycarbonyl, lower alkenoxycarbonyl, lower alkynoxycarbonyl, carbamoyl, mono(-lower alkyl)carbamoyl, di(lower alkyl)carbamoyl or N-heterocyclylcarbonyl, $R_5$, $R_7$, $R_{10}$, $R_{11}$, $R_{12}$ and $R_{13}$ are hydrogen or fluorine, with the proviso that at least one of $R_5$, $R_7$, $R_{10}$, $R_{11}$, $R_{12}$ or $R_{13}$ is fluorine or at least one of $R_6$ or $R_8$ is trifluoro methyl, or pharmaceutically acceptable salts thereof.

As used herein "lower alkyl" means alkyl groups which contain from 1 to 6 carbon atoms, e.g., methyl, ethyl, propyl, isopropyl, 2-methyl-propyl and the like, "lower alkoxy" means alkoxy groups which contain from 1 to 6 carbon atoms, e.g., methoxy, ethoxy, isopropoxy and the like, the terms "alkoxymethyl" and "alkoxycarbonyl" include straight chain or branched-chain alkoxy groups having from 1 to 20 carbon atoms, e.g., methoxy, ethoxy, isopropoxy or cetyloxy. Preferred, however, are those alkoxy groups containing from 1 to 6 carbon atoms. The said alkoxy group can be unsubstituted or substituted by functional groups, for example, by nitrogen containing groups such as by substituted or alkyl-substituted amino or morpholino groups or by a piperidyl or pyridyl group. The terms "lower alkenoxycarbonyl" and "lower alkynoxycarbonyl" include alkenoxy and alkynoxy groups having from 1 to 6 carbon atoms, e.g., allyloxy, propargyloxy and the like.

The alkanoyloxy groups present in the alkanoyloxymethyl group are derived from alkanecarboxylic acids containing from 1 to 20 carbon atoms, e.g., acetic acid, propionic acid, pivalic acid, palmitic acid, stearic acid and the like. The preferred group of alkanecarboxylic acids are lower alkanecarboxylic acids which contain from 1 to 6 carbon atoms. The carbamoyl groups within the scope of this invention can be monosubstituted or disubstituted by straight chain or branched chain lower alkyl groups, e.g., methyl, ethyl, isopropyl and the like. Examples of such substituted carbamoyl groups are the methyl carbamoyl, dimethylcarbamoyl, and diethylcarbamoyl. The term "N-heterocyclyl" includes 5-membered or 6-membered heterocyclic groups which, in addition to one nitrogen may contain a second nitrogen, oxygen or sulfur. Of the heterocyclic rings, piperidino, morpholino, thiomorpholino and pyrrolidino are preferred. "Pharmaceutically acceptable salts" means alkali metal salts, e.g., sodium or potassium. All formulas depicted include cis/trans and all trans isomers of the double bonds on the polyene side chains.

Examples of the polyene compounds within the scope of this invention are:

9-(4-methoxy-2,3,6-trimethylphenyl)-2-fluoro-3,7-dimethyl-2(Z),4(E),6(E),8(E)-nonatetraenoic acid ethyl ester, 9-(4-methoxy-2,3,6-trimethylphenyl)-2-fluoro-3,7-dimethyl-2(Z),4(E),6(Z),8(E)-nonatetraenoic acid ethyl ester, 9-(4-methoxy-2,3,6-trimethylphenyl)-6-fluoro-3,7-dimethyl-2(E),4(E),6(Z),8(E)-nonatetraenoic acid methyl ester, 9-(4-methoxy-2,3,6-trimethylphenyl)-6-fluoro-3,7-dimethyl-2(Z),4(E),6(Z),8(E)-nonatetraenoic acid methyl ester, 9-(4-methoxy-2,3,6-trimethylphenyl)-6-fluoro-3,7-dimethyl-2(E),4(E),6(E),8(E)-nonatetraenoic acid methyl ester, 9-(4-methoxy-2,3,6-trimethylphenyl)-4-fluoro-3,7-dimethyl-2(E),4(E),6(E),8(E)-nonatetraenoic acid ethyl ester, 9-(4-methoxy-2,3,6-trimethylphenyl)-4-fluoro-3,7-dimethyl-2(E),4(Z),6(E),8(E)-nonatetraenoic acid ethyl ester, 9-(4-methoxy-2,3,6-trimethylphenyl)-3-methyl-7-trifluoromethyl-2(E),4(E),6(E),8(E)-nonatetraenoic acid methyl ester, 9-(4-methoxy-2,3,6-trimethylphenyl)-3,7-dimethyl-5-fluoro-2,4,6,8-nonatetraenoic acid ethyl ester, 9-(4-methoxy-2,3,6-trimethylphenyl)-3,7-dimethyl-8-fluoro-2,4,6,8-nonatetraenoic acid methyl ester, 9-(4-methoxy-2,3,6-trimethylphenyl)-3-trifluoromethyl-7-methyl-2,4,6,8-nonatetraenoic acid ethyl ester, 9-(4-methoxy-2,3,6-trimethylphenyl)-8-fluoro-3,7-dimethyl-2(E),4(E),6(E),8(Z)-nonatetraenoic acid methyl ester, 9-(4-methoxy-2,3,6-trimethylphenyl)-3-trifluoromethyl-7-methyl-2(E),4(E),6(E),8(E)-nonatetraenoic acid ethyl ester, methyl 9-(4-methoxy-2,3,6-trimethylphenyl)-3,7-dimethyl-5-fluoro-2(E),4(Z),6(Z,E),8(E)-nonatetraenoate, ethyl 2(E),4(E),6(E),8(Z)-3,7-dimethyl-9-fluoro-9-(4-methoxy-2,3,6-trimethylphenyl)-nonatetraenoate, ethyl 2(E),4(E),6(E),8(E)-3,7-dimethyl-9-fluoro-9-(4-methoxy-2,3,6-trimethylphenyl)-nonatetraenoate, 9-(4-methoxy-2,3,6-trimethylphenyl)-3,7-dimethyl-6-fluoro-2(E),4(E),6(Z),8(E)-nonatetraenal, 9-(4-methoxy-2,3,6-trimethylphenyl)-3,7-dimethyl-6-fluoro-2(E),4(E),6(E),8(E)-nonatetraenal, 9-(4-methoxy-2,3,6-trimethylphenyl)-3,7-dimethyl-4-fluoro-2(E),4(Z),6(E),8(E)-nonatetraenoic acid, 9-(4-methoxy-2,3,6-trimethylphenyl)-3,7-dimethyl-4-fluoro-2(E),4(Z),6(E),8(E)-nonatetraenoic acid ethyl amide, ethyl 2(E,Z),4(Z),6(E),8(E)-2,4-difluoro-3,7-dimethyl-9-(4-methoxy-2,3,6-trimethylphenyl)-nonatetraenoate, ethyl 2(Z),4(E),6(Z),8(E)-2,6-difluoro-3,7-dimethyl-9-(4-methoxy-2,3,6-trimethylphenyl)-nonatetraenoate, ethyl 2(E),4(Z),6(Z),8(E)-3,7-dimethyl-4,6-difluoro-9-(4-methoxy-2,3,6-trimethylphenyl)-nonatetraenoate.

The compounds represented by formula I are pharmacodynamically valuable. They can be used for the topical and systemic therapy of benign and malignant neoplasia and of premalignant lesions as well as for the systemic and topical prophylaxis of these conditions.

The compounds of this invention are relatively non-toxic. The tumor-inhibition action of the compounds is significant. In the papilloma test, tumors induced with dimethylbenzanthracene and croton oil regress.

The following Table illustrates the activity and toxicity of the compounds of this invention:

TABLE I

| Example | Hypervitaminosis effective dose mg/kg/day | Papilloma Effect Dose mg/kg/wk | Effect ± % regression |
|---|---|---|---|
| 4 | 12.5 | 50 | −37 |
| 5 | 100 | 400 | −65 |
| 6 | >200 | 800 | −4 |
| 9 | 50 | 200 | −79 |
|  |  | 100 | −60 |
|  |  | 50 | −35 |
|  |  | 25 | −24 |
| 10 |  | 200 | −28 |
| 11 | >200 | 400 | −20 |
| 18 | >200 | 400 | −25 |
| 12 (E,E,E cpd) | >200 | 400 | −51 |
| 12, 23 (E,Z,E,E cpd) | 50, 100 (mice) 200 i.p. (rats) >200 p.o. | 400 200 100 50 25 | −91 −73 −72 −61 −71 −41 |
| 30 | >200 | 400 | −34 |
| 32 | >200 | 400 | −8 |

The compounds represented by formula I can be used as medicaments in the form of pharmaceutical preparations which contain them in association with a compatible carrier material.

Pharmaceutical preparations for systemic administration can be prepared, for example, by adding a compound represented by formula I as the active ingredient to pharmaceutically acceptable, non-toxic, inert, solid or liquid carriers which are usual in such preparations. The pharmaceutical preparations can be administered enterally, parenterally or topically. Suitable preparations for enteral administration are, for example, tablets, capsules, dragees, syrups, suspension, solutions and suppositories. Suitable pharmaceutical preparations for parenteral administration are infusion solutions.

The dosages in which the compounds are administered can be varied according to the mode and route of administration and according to the requirements of the patient. For example, the compounds can be administered in amounts of from 25 mg. to 100 mg. daily in one or more dosages.

The pharmaceutical preparations can contain in addition to the active compounds of this invention, pharmaceutically acceptable inert or pharmacodynamically active additives. Tablets or granules, for example, can contain a series of pharmaceutically acceptable binders, fillers, carrier materials or diluents. Liquid preparations can, for example, take the form of sterile water-miscible solutions. Capsules can contain a pharmaceutically acceptable filler or thickener. Furthermore, pharmaceutically acceptable flavor improving additives and pharmaceutically acceptable substances commonly used as preservatives, stabilizers, moisture retainers or emulsifiers, salts for varying the osmotic pressure, buffers and other pharmaceutically acceptable additives can also be present in the pharmaceutical preparations.

The aforementioned pharmaceutically acceptable carrier materials and diluents are well known to the pharmaceutical compounding art and can be organic or inorganic substances such as water, gelatin, lactose, magnesium stearate, talc, gum arabic, polyalkyleneglycols and the like. It is, of course, a prerequisite that all adjuvants used in the preparation of the pharmaceutical preparations are non-toxic and pharmaceutically acceptable.

For topical administration, the compounds of this invention are expediently made up in the form of salves, tinctures, creams, solutions, lotions, sprays, suspensions and the like. Ointments, creams and solutions are preferred. These pharmaceutical preparations for topical administration can be prepared by mixing a compound of this invention as the active ingredient with pharmaceutically acceptable non-toxic, inert, solid or liquid carriers which are customary in such preparations and which are suitable for topical administration.

A conventional pharmaceutically acceptable antioxidant, e.g., tocopherol, N-methyl-γ-tocopheramine butylated hydroxyanisole or butylated hydroxytoluene can also be incorporated into the pharmaceutical preparations containing the compounds of this invention.

The compounds represented by formula I can occur as cis/trans mixtures which can be separated into the cis and trans compounds or isomerised to the all trans compound by conventional means, are prepared as follows.

Reacting a compound represented by the formula

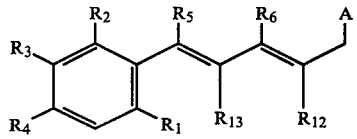

II with a compound represented by the formula

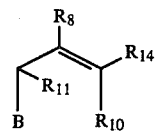

III wherein in formulas II and III, one of A and B is oxo and the other is either a triarylphosphonium represented by the formula $-P[Y]_3^{\oplus}Z^{\ominus}$, wherein Y is aryl and Z is the anion of an inorganic or organic acid; or a dialkoxyphosphinoxy represented by the formula

wherein X is alkoxy; $R_1$, $R_2$, $R_3$, $R_4$, $R_5$, $R_6$, $R_8$, $R_{10}$, $R_{11}$, $R_{12}$ and $R_{13}$ have the same meanings given in formula I; $R_{14}$ is alkoxymethyl, dialkoxymethyl, alkanoyloxymethyl, alkoxycarbonyl, alkenoxycarbonyl or alkynoxycarbonyl when B is the oxo group or $R_{14}$ is formyl, hydroxymethyl, alkoxymethyl, dialkoxymethyl, carboxyl, alkoxycarbonyl, alkenoxycarbonyl or alkynoxycarbonyl when B is triarylphosphonium or dialkoxyphosphinoxy.

In addition the 5-fluoro compounds represented by formula I can be prepared as follows:

Oxidizing with manganese dioxide a compound represented by the formula

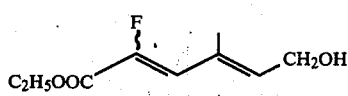

[said compound is prepared by reacting

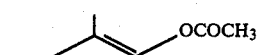

with

followed by selective hydrolysis] to form the corresponding aldehyde represented by the formula

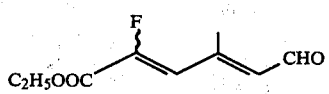

then converting the aldehyde group to an acetal by reaction with methanol in the presence of ammonium chloride to form a compound represented by the formula

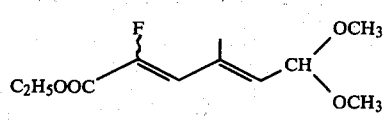

which compound is converted to an aldehyde represented by the formula

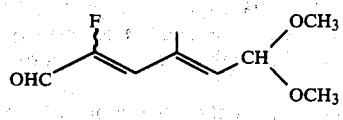

by reaction with diisobutyl aluminum hydride in the cold (about −70° C.).

The aldehyde is then reacted a phosphonium chloride represented by the formula

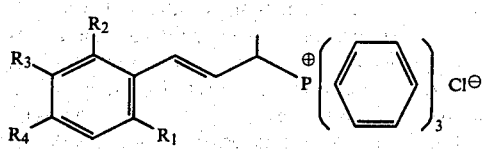

to form, after acidic hydrolysis, the aldehyde represented by the formula

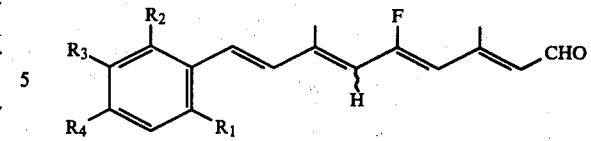

wherein $R_1$, $R_2$, $R_3$ and $R_4$ are the same as in formula I.

The aldehyde is then converted to the corresponding ester by conventional means.

Additional process steps can be performed in various optional sequences, e.g., esterifying or amidating a carboxylic acid obtained according to the above process steps, or hydrolyzing or amidating a carboxylic acid ester obtained according to the above process steps or reducing a carboxylic acid or carboxylic acid ester obtained according to the above process steps to the corresponding alcohol and optionally etherifying or esterifying said alcohol, or saponifying an alcohol ester or hydrolysis of an acetal obtained according to the above process steps, or oxidizing an alcohol or alcohol ester obtained according to the above process steps.

The aryl groups denoted by Y in the triaylphosphonium group used in the process of this invention include all known aryl groups, but preferably includes mononuclear aryl groups such as the phenyl group, lower alkyl-phenyl or lower alkoxy-phenyl groups, e.g., tolyl, xylyl, mesityl and p-methoxyphenyl.

Of the inorganic acid anions denoted by Z in the triarylphosphonium group used in the process of this invention, the chlorine, bromine, iodine or hydrosulphate ion are preferred. The preferred organic acid anion is the tosyloxy ion.

The alkoxy groups denoted by X in the dialkoxyphosphinoxy group used in the process of this invention are preferably lower alkoxy groups containing from 1 to 6 carbon atoms, most preferably the methoxy and ethoxy groups.

9-Fluoro compounds represented by formula I can be prepared by the following reaction sequence:

Converting an aldehyde represented by the formula

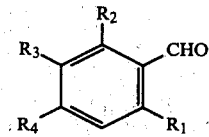

to the alcohol by conventional means, then brominating by conventional means to form a compound represented by the formula

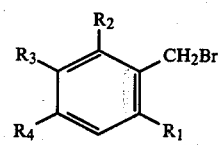

which is then reacted with triethyl phosphite to form the phosphonate represented by formula

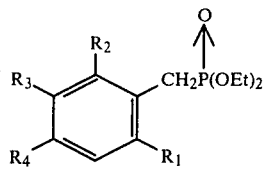

which is then fluorinated by reaction in an anhydrous organic solvent with perchlorylfluoride in the presence of n-butyl lithium to form the intermediate represented by the formula

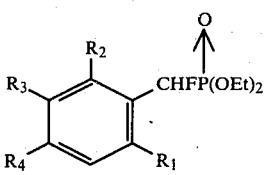

The intermediate is not isolated but is combined with all trans-3-methyl-7-formyl-2,4,6-octatrienoic acid ethyl ester in an organic solvent and then added to a cold(−70° C.) solution of lithium diisopropylamide. The product is worked up and the cis and trans isomers are separately isolated. The products are represented by the following formulas:

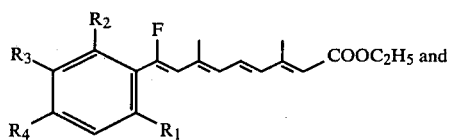

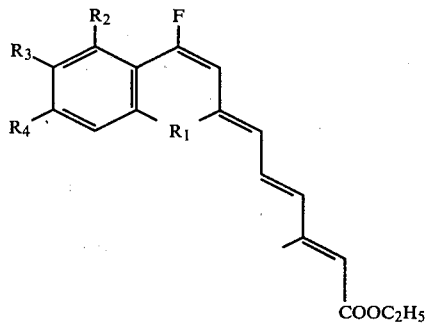

wherein $R_1$, $R_2$, $R_3$ and $R_4$ are the same as in formula I.

The compounds represented by formula I can also be prepared by lengthening the side chain of an appropriate aldehyde or ketone in increments of two carbon atoms until the desired chain length is achieved using the former reaction as described hereinafter. Initially the added carbons contain either a fluorine or trifluoromethyl. Thus, for example, a compound represented by the formulas

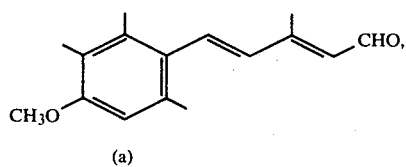

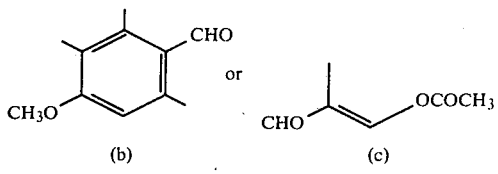

are reacted with

to result in a compound with a fluorinated carbon side chain, i.e.,

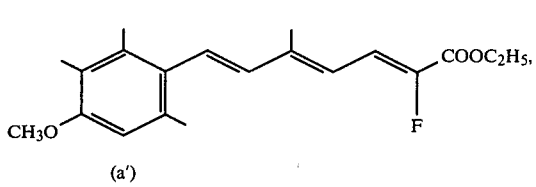

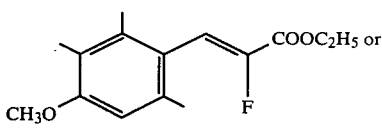

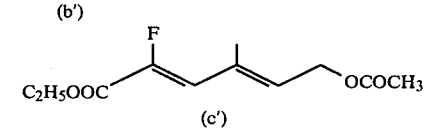

respectively.

Compounds (a′) and (b′) are subsequently converted to the corresponding carboxylic acids and then to the corresponding methyl ketone and subjected to further Horner reactions utilizing

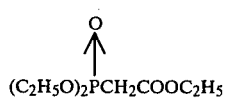

to lengthen the side chain of the desired number of carbon atoms. This sequence is repeated until the desired chain length is reached. The carboxylic acids are converted to the methyl ketones by means of methyl lithium.

The compounds within the scope of formula II, some of which are novel, can be prepared, for example, by treating an appropriately-substituted benzene with a formylating agent in a conventional manner in the presence of a Lewis acid and condensing the resulting substituted benzaldehyde with acetone in a conventional manner. The resulting 4-(substituted phenyl)-but-3-en-2-one is subsequently converted into a 3-methyl-5-(substituted phenyl)-penta-2,4-dien-1-oic acid ethyl ester or a 2-fluoro-3-methyl-5-(substituted phenyl)-penta-2,4-dien-1-oic acid ethyl ester by condensation with diethylphosphonoacetic acid ester or with diethyl fluoro phosphonoacetic acid ester in a conventional manner. The carboxylic acid ester obtained is reduced in a conventional manner using diisobutyl aluminum hydride or bis-(2-methoxy-ethoxy)sodium aluminum hydride. The resulting 3-methyl-5-(substituted phenyl)-penta-2,4-dien-1-ol or 2-fluoro-3-methyl-5-(substituted phenyl)-penta-2,4-dien-1-ol is treated with an oxidizing agent, e.g., manganese dioxide in an organic solvent such as acetone or methylene chloride, to give a compound with the scope of formula II in which A is the oxo group.

Compounds represented by formula II in which A is triarylphosphonium group or a dialkoxyphosphinoxy group can be prepared by halogenating a 3-methyl-5-(substituted phenyl)-penta-2,4-dien-1-ol or a 2-fluoro-3-methyl-5-(substituted phenyl)-penta-2,4-dien-1-ol in a conventional manner, e.g., by treatment with a phosphorus tri- or pentahalide, and reacting the resulting halide with a triarylphosphine or with a trialkylphosphite.

Compounds within the scope of formula II wherein a trifluoro methyl group on the side chain can be prepared, for example, by treating an appropriately substituted benzaldehyde with a propargyl Grignard reagent, i.e., $CF_3C\equiv C-MgBr$, and rearranging the resulting propargyl compound by treating it with mercuric sulfate in acidic medium according to the Meyer Schuster rearrangement reaction.

Compounds within the scope of formula II can also be prepared by reacting compounds of formula III with a compound of formula IV

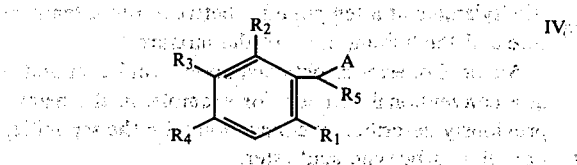

IV wherein $R_1, R_2, R_3, R_4$ and $R_5$ are as defined in formula I and A is as defined in formula II.

If A is oxo, the starting material can be reacted with a compound of formula III where B is either a triarylphosphonium or dialkoxyphosphinoxy as in formula III to produce a novel compound of formula V

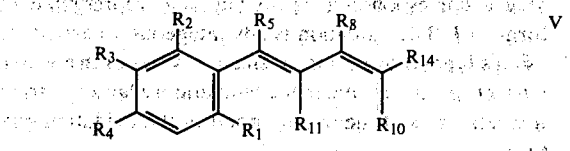

V wherein $R_1, R_2, R_3, R_4, R_5, R_8, R_{10}, R_{11}$ and $R_{14}$ are the same as in formulas II and III, wherein the proviso of formula I is waived since the novel intermediate compounds are not required to have fluorine or trifluoromethyl.

Where B of formula III is oxo, then A of formula IV is a triarylphosphonium or dialkoxyphosphinoxy as in formula II.

The preparation of the compounds represented by formula III are documented in the literature.

The reaction of a compound represented by formula II with a compound represented by formula III yields a compound represented by formula I. The reaction is carried out by either a Wittig or Horner reaction.

According to the Wittig procedure, the respective starting materials are reacted together in the presence of an acid-binding agent, e.g. an alkali metal alcoholate such as sodium methylate or an alkylene oxide which may be alkyl-substituted, preferably ethylene oxide or 1,2-butylene oxide, in a solvent, e.g., a chlorinated hydrocarbon such as methylene chloride or dimethylformamide or without a solvent at a temperature between room temperature and the boiling point of the reaction mixture.

According to the Horner procedure, the reaction is carried out with the aid of a base and preferably in the presence of an inert organic solvent, e.g., using sodium hydride in benzene, toluene, dimethylformamide, tetrahydrofuran, dioxane or 1,2-dimethoxyethane, or using an alkali metal alcoholate in an alkanol such as sodium methylate in methanol, at a temperature between 0° C. and the boiling point of the reaction mixture.

Difluoro compounds represented by formula I can be prepared as follows:

(a) Reacting a compound represented by the formula

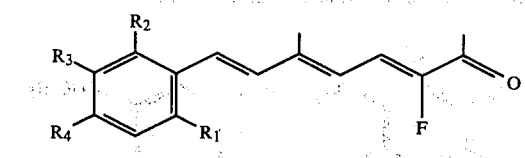

with a phosphono compound represented by the formula

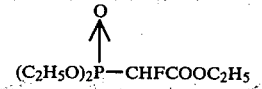

$(C_2H_5O)_2P-CHFCOOC_2H_5$ in an organic solvent in the presence of sodium hydride to produce a compound represented by the formula

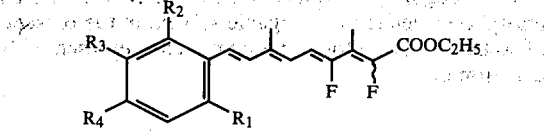

wherein $R_1, R_2, R_3$ and $R_4$ are the same as in formula I.

(b) Reacting a compound represented by the formula

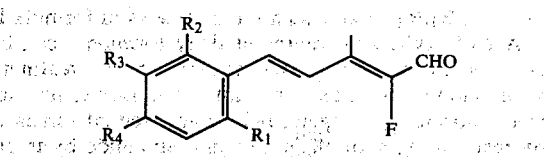

with a compound represented by the formula

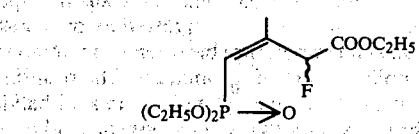

in an organic solvent in the presence of sodium hydride to produce a compound represented by the formula

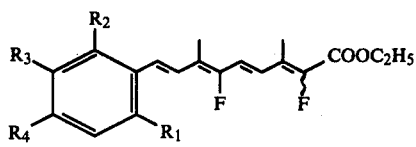

wherein $R_1, R_2, R_3$ and $R_4$ are the same as in formula I.

(c) Reacting a compound represented by the formula

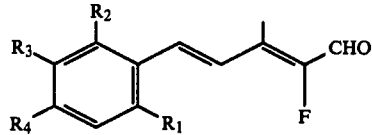

with triethyl phosphonofluoroacetate in an organic solvent in the presence of sodium hydride to form a compound represented by the formula

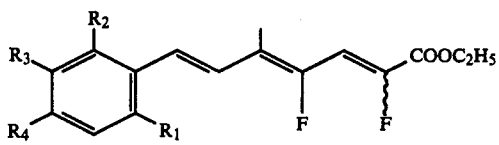

which in turn is converted to corresponding acid which when reacted with methyl lithium in the cold ($-75°$ C.) yielded a compound represented by the formula

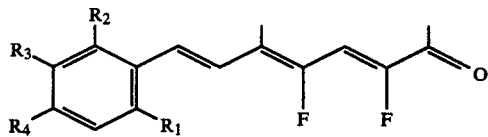

The foregoing compound, when reacted with triethyl phosphonoacetate in an organic solvent in the presence of sodium hydride formed a compound represented by the formula

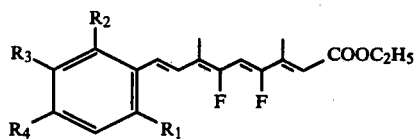

wherein $R_1, R_2, R_3$ and $R_4$ are the same as in formula I.

A carboxylic acid represented by formula I can be converted in a conventional manner, e.g., by treatment with thionyl chloride, preferably in pyridine, into an acid chloride which then can be converted into an ester by reaction with an alkanol or into an amide by treatment with ammonia or an amine.

A carboxylic acid ester represented by formula I can be hydrolyzed to a carboxylic acid in a conventional manner, for example, by treatment with alkali, especially aqueous-alcoholic sodium hydroxide or potassium hydroxide at a temperature between room temperature and the boiling point of the mixture. The resulting carboxylic acid can then be amidated via an acid halide as set forth above. Alternatively, a carboxylic acid ester can be directly amidated as described hereinafter.

A carboxylic acid ester represented by formula I can be converted directly into a corresponding amide by treatment with lithium amide. This treatment is advantageously carried out at room temperature.

A carboxylic acid or a carboxylic acid ester represented by formula I can be reduced to a corresponding alcohol represented by formula I in a conventional manner. The reduction is advantageously carried out using a metal hydride or an alkyl metal hydride in an inert solvent. Examples of hydrides which have proved to be especially suitable are mixed metal hydrides such as lithium aluminum hydride or bis-(2-methoxy-ethoxy)-sodium aluminum hydride. Suitable inert solvents are, inter alia, ether, tetrahydrofuran or dioxane when lithium aluminum hydride is used and ether, hexane, benzene or toluene when diisobutylaluminum hydride or bis-(2-methoxy-ethoxy)-sodium aluminum hydride is used.

An alcohol represented by formula I can be etherified with an alkyl halide, e.g., ethyl iodide, for example, in the presence of a base, preferably sodium hydride, in an organic solvent such as dioxane, tetrahydrofuran, 1,2-dimethoxyethane or dimethylformamide at a temperature between 0° C. and room temperature.

An alcohol represented by formula I can be esterified by treatment with an alkanoyl halide or anhydride, conveniently in the presence of a base, e.g., pyridine or triethylamine at a temperature between room temperature and the boiling point of the mixture.

An alcohol ester as obtained above can be saponified in a conventional manner, for example, in the manner previously described in connection with the saponification of a carboxylic acid ester.

An acetal as obtained above can be hydrolyzed in a conventional manner by treatment with a proton donator in an inert solvent, e.g., using hydrochloric acid in tetrahydrofuran.

An alcohol represented by formula I or an ester thereof can be oxidized in a conventional manner to give a corresponding carboxylic acid represented by formula I. The oxidation is advantageously carried out using silver (I) oxide and an alkali in water or in a water-miscible organic solvent at a temperature between room temperature and the boiling point of the oxidation mixture.

An alcohol represented by formula I can be oxidized to an aldehyde by treatment, for example, with manganese dioxide.

The most efficient means for producing the compounds represented by formula I in which $R_{11}$ or $R_{12}$ is fluorine are as follows:

Reacting an aromatic triphenyl phosphonium chloride represented by the formula

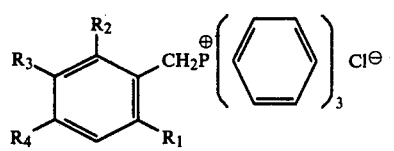

wherein $R_1, R_2, R_3$ and $R_4$ are the same as in formula I with a compound represented by the formula

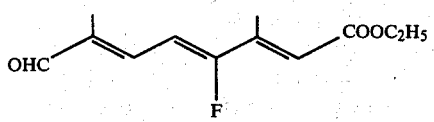

or a compound represented by the formula

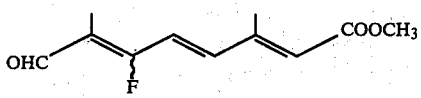

in an organic solvent.

The 4-fluoro octatrienoate is prepared by reacting triethyl phosphonofluoroacetate with 4,4-dimethoxy-3-methyl-2-butenal and the resulting reaction product, ethyl(E/Z,E)-2-fluoro-6,6-dimethoxy-5-methyl-2,4-hexadienoate, is treated with lithium hydroxide to form the lithium salt which is then treated with methyl lithium to form (E/Z,E)-3-fluoro-7,7-dimethoxy-6-methyl-3,5-heptadien-2-one. The latter compound is then reacted with triethyl phosphonoacetate to form ethyl-(E,E/Z,E)-4-fluoro-3,7-dimethyl-8-oxo-2,4,6-octatrienoate. Treatment with iodine results in the 4-fluoro octatrienoate depicted.

The 6-fluoro octatrienoate is prepared by reacting triethyl phosphono fluoroacetate with glyoxal dimethyl acetal and the resulting reaction product, a mixture of ethyl E and Z-2-fluoro-4,4-dimethoxy-3-methyl-2-butenoate, is reduced with di-isobutyl aluminum hydride in the cold to form Z-2-fluoro-3-methyl-4,4-dimethoxy-2-buten-1-al. The latter compound is then reacted via a Horner reaction with a compound of the formula

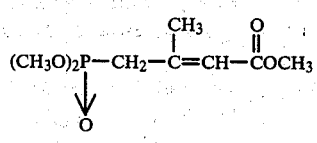

or via a Wittig reaction with

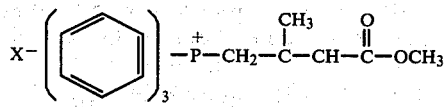

wherein X is halogen to form a compound of the formula

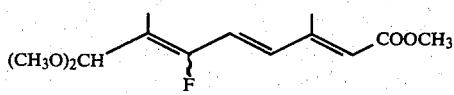

The latter compound is then treated with hydrochloric acid and diethyl ether to form the 6-fluoro octatrienoate depicted.

The compounds of the formulas VIII, VIII-A and VIII-B as well as ethyl(E/Z,E)-2-fluoro-6,6-dimethoxy-5-methyl-2,4-hexadienoate and ethyl E and Z-2-fluoro-4,4-dimethoxy-3-methyl-2-butenoate have been shown for illustration as specific esters. It is apparent that any lower alkyl ester can be prepared and utilized in accordance with this invention. These specific esters can be hydrolyzed to the corresponding acid and reesterified by conventional means.

EXAMPLE 1

5-(4-methoxy-2,3,6-trimethylphenyl)-3-methyl-2(Z,E),-4(E)-pentadienoic acid methyl ester 4.92 G. of sodium hydride (50% oil dispersion, 0.103 mol) which was washed with 3×50 ml. of pentane was added to a 1.0 l, 3-necked round-bottomed flask. 330 Ml. of ethylene glycol dimethyl ether (glyme) (distilled over lithium aluminum hydride) was added and the mixture was cooled to 0° C. and 20.08 g. (0.111 mol) of trimethylphosphono acetate was slowly added. The resulting mixture was allowed to warm to 23° C. and mechanically stirred at this temperature for 2.0 hrs. under argon. 20.0 G. (0.092 mol) of 4-(4-methoxy-2,3,6-trimethylphenyl)-3-buten-2-one in 50 ml. of ethyleneglycol dimethyl ether was added dropwise to the resulting thick white paste. The resulting mixture was stirred at 23° C. for 45 min. and then refluxed for 2½ hours. It was then cooled in an ice-bath and the content was poured portionwise onto 1.2 l. of ice-water. The resulting solution was then neutralized to pH 6-7 with 2NHCl and then extracted with methylene chloride (3×300 ml.). The combined methylene chloride extract was washed with water (3×200 ml.), brine (1×300 ml.), and dried over anhydrous $Na_2SO_4$. The solvent was evaporated in vacuo to give an orange-yellow oil which was quickly chromatographed on 250 g. of silica gel. Elution with chloroform affored 5-(4-methoxy-2,3,6-trimethylphenyl)-3-methyl-2(Z,E),,4(E)-pentadienoic acid methyl ester as a light orange colored oil. The ratio of isomers was approximately 2:3 (2Z:2E) as determined by nmr analysis.

EXAMPLE 2

5-(4-methoxy-2,3,6-trimethylphenyl)-3-methyl-2(Z,E),-4(E)-pentadien-1-ol 40.0 G. (0.146 mol) of 5-(4-methoxy-2,3,6-trimethylphenyl)-3-methyl-2(Z,E),4(E)-pentadienoic acid acid, methyl ester in 500 ml. of dry ether was added to a 2.0 l. three-necked round-bottomed flask. The resulting solution was cooled to −73° C. and, under argon, 106 ml. of diisobutylaluminum hydride (1.5 molar in hexane, 0.160 mol) was added. The resulting reaction mixture was stirred at −73° C. for ½ hr. and monitored by thin layer chromatography. More diisobutylaluminum hydride (100 ml., 0.15 mol) was added again in three portions every half an hour, with stirring at −73° C. Thin layer chromatography showed only trace of starting material present. The reaction mixture was gradually warmed to −30° C. and 250 ml. of methanol-water (1:1) was slowly added with stirring. Water (500 ml.) was then added slowly and the temperature was maintained at ca 10° C. until the formation of precipitate ceased. The mixture was filtered over celite and washed several times with ether. The ethereal phase was separated and washed with 1NHCl (3×100 ml.), saturated brine (3×100 ml.) and dried over anhydrous magnesium sulfate. The solvent was evaporated in vacuo to give 5-(4-methoxy-2,3,6-trimethylphenyl)-3-methyl-2(Z,E),4(E)-pentadien-1-ol as a yellow oil. An analytical sample showed isomeric ratio of 2E and 2Z being ca 2:1.

EXAMPLE 3

5-(4-methoxy-2,3,6-trimethylphenyl)-3-methyl-2(E),-4(E)-pentadien-1-al and 5-(4-methoxy-2,3,6-trimethylphenyl)-3-methyl-2(Z),4(E)-pentadien-1-al 306 G. (3.5 mol) of manganese dioxide and 750 ml. of methylene chloride were added to a 2.0 l. three-necked round-bottomed flask. The flask was flushed with argon. To the above well stirred mixture was added 66 g. (0.268 mol) of 5-(4-methoxy-2,3,6-trimethylphenyl)-3-methyl-2(Z,E),4(E)-pentadien-1-ol in 500 ml. of methylene chloride. The resulting mixture was mechanically stirred at 23° C., under argon, for four days. The resulting mixture was filtered over celite and the cake was washed with 2.0 l. of methylene chloride. The solvent was evaporated in vacuo to yield a crude oil. This material was purified first by column chromatography on silica gel (800 g.) and then by preparative high pressure chromatography. This procedure led to the isolation of 5-(4-methoxy-2,3,6-trimethylphenyl)-3-methyl-2(Z),4(E)-pentadien-1-al as the less polar component, which on recrystallization from ether-petroleum ether gave light yellow crystals, m.p. 82°–85° C. Further elution of the column gave 5-(4-methoxy-2,3,6-trimethylphenyl)-3-methyl-2(E),4(E)-pentadien-1-al, as light yellow crystals, m.p. 61°–63° C. from ether-petroleum ether.

EXAMPLE 4

9-(4-methoxy-2,3,6-trimethylphenyl)-2-fluoro-3,7-dimethyl-2(Z),4(E),6(E),8(E)-nonatetraenoic acid ethyl ester 5.05 G. (0.0179 mol) of 4-diethoxyphosphinyl-2(Z,E)-fluoro-3-methyl crotonic acid ethyl ester in 10 ml. of ethylene glycol dimethyl ether was added dropwise to a cold (0°–5°) suspension of 0.83 g. (0.0173 mol) of sodium hydride (50% oil dispersion) which had been washed with pentane to remove the oil, in 50 ml. of ethylene glycol dimethyl ether. The resulting mixture was stirred at 23° C. for 1.0 hr. To this dark brown mixture was then added 4.35 g. (0.0178 mol) of 5-(4-methoxy-2,3,6-trimethylphenyl)-3-methyl-2(E),4(E)-pentadien-1-al in 20 ml. of ethylene glycol dimethyl ether. The resulting reaction mixture was stirred at 23° C. under argon for 2.0 hrs. It was then poured into 250 ml. of ice-water, acidified to pH 4 with 1NHCl and extracted with methylene chloride (3×200 ml.). The $CH_2Cl_2$ extracts were combined, washed with water (2×200 ml.) and saturated brine (2×150 ml.) and dried ($MgSO_4$). Evaporation of solvent to dryness in vacuo yielded crude crystalline material which was purified by column chromatography on 250 g. of silica gel. Elution with ether-petroleum ether (5:95) gave a crystalline substance, which on recrystallization from methylene chloride-petroleum ether yielded pure 9-(4-methoxy-2,3,6-trimethylphenyl)-2-fluoro-3,7-dimethyl-2(Z),4(E),6(E),8(E)-nonatetraenoic acid ethyl ester as yellow crystal m.p. 140°–143° C.

EXAMPLE 5

9-(4-methoxy-2,3,6-trimethylphenyl)-2-fluoro-3,7-dimethyl-2(Z),4(E),6(Z),8(E)-nonatetraenoic acid ethyl ester 5.52 G. (0.0196 mol) of 4-diethoxyphosphinyl-2(Z,E)-fluoro-3-methyl crotonic acid ethyl ester in 10 ml. of ethylene glycol dimethyl ether was added dropwise to a cold (0°–5°) suspension of 0.984 g. (0.0205 mol) of sodium hydride (50% oil dispersion), which had been washed with pentane to remove the oil, in 50 ml. of ethylene glycol dimethyl ether. The resulting mixture was stirred at 23° C. for 1.0 hr., 4.80 g. (0.0196 mol) of 5-(4-methoxy-2,3,6-trimethylphenyl)-3-methyl-2(Z),4(E)-pentadien-1-al in 20 ml. of ethylene glycol dimethyl ether was then added to the resulting dark brown suspension. The resulting reaction mixture was stirred at 23° C. under argon for 2.0 hrs. and then poured into 250 ml. of ice-water. It was worked up as described in Example 4 to yield a crude oily product which was quickly chromatographed on 250 g. of silica gel. Elution with ether-petroleum ether (5:95) yielded an oily substance which upon further purification by five recrystallizations from petroleum ether yielded 9-(4-methoxy-2,3,6-trimethylphenyl)-2-fluoro-3,7-dimethyl-2(Z),4(E),6(Z),8(E)-nonatetraenoic acid ethyl ester as yellow crystals m.p. 103°–113° C. High pressure liquid chromatographic analysis of this substance indicated a purity of approximately 90%.

EXAMPLE 6

Ethyl 5-[4-methoxy-2,3,6-trimethylphenyl]-2(Z,E)-fluoro-3-methyl-2,4(E)-pentadienoate 14.4 G. of sodium hydride (50% oil dispersion, 0.30 mol) was placed into a 2.0 l. three-necked flask under argon and washed with 100 ml. of pentane. Ethylene glycol dimethyl ether (250 ml., distilled from lithium aluminum hydride) was then added and the flask was cooled in an ice-bath. The resulting mixture was well stirred and 72.7 g. (0.30 mol) of triethylfluorophosphono-acetate in 80 ml. of ethylene glycol dimethyl ether was added dropwise under argon over a period of 30 min. The resulting mixture was again stirred at 23° C. under argon for two more hours and the color became brown. More ethylene glycol dimethyl ether (70 ml.) was added. Under vigorous stirring 65.4 g. (0.30 mol.) of 4-(4-methoxy-2,3,6-trimethylphenyl)-3-buten-2-one in 200 ml. of ethylene glycol dimethyl ether was then added dropwise at 23° over a period of 40 min. An exothermic reaction was observed and a brown colored syrupy precipitate began appearing. The reaction was further stirred at 23° C. for 1.0 hr. and at 52°–55° C. for 4.0 hrs. The flask was then cooled in an ice-bath and ice-water (1.0 l.) was added, the solution was adjusted to ~pH 4–5 with 1N HCl and extracted with methylene chloride (3×250 ml.). The combined $CH_2Cl_2$ extract was washed with water (3×200 ml.) and dried over anhydrous $MgSO_4$. Evaporation of solvent to dryness in a rotary evaporator at reduced pressure yielded brown colored oil which was purified by column chromatography on 800 g. of silica gel. Elution with ether:-petroleum ether (30°–60° C.) (5:95) yielded pure ethyl 5-[4-methoxy-2,3,6-trimethylphenyl]-2(Z,E)-fluoro-3-methyl-2,4(E)-pentadienoate as a mixture of isomers in a ratio approximately 2(Z):2(E)=3:2.

EXAMPLE 7

5-[4-methoxy-2,3,6-trimethylphenyl]-2(Z,E)-fluoro-3-methyl-2,4(E)-pentadien-1-ol 57.5 G. (0.188 mol) of ethyl 5-[4-methoxy-2,3,6-trimethylphenyl]-2(Z,E)-fluoro-3-methyl-2,4(E)-pentadienoate was dissolved in absolute ether (1.20 l.) and cooled in a dry ice-acetone bath to −70° C., under argon with stirring. (Crystallization occurred). Diisobutylaluminum hydride (250 ml., ~1.5 molar in hexane) was then added dropwise over a period of 30 min. in such a rate that the internal temperature was maintained at −65° C. to −70° C. The reaction was monitored by thin layer chromatography which indicated the presence of starting ester. More diisobutylaluminum hydride (125 ml.) was then added again over a period of 2.0 hrs. and TLC showed no more starting material present. Methanolwater (1:1, 500 ml.) was added slowly and the temperature of the reaction mixture was stirred at 5° to 10° C. for a few minutes until the formation of precipitates stopped in an exothermic reaction. The precipitate was filtered off through celite and washed with 4×800 ml. of ether. The combined filtrate (ca. 4.5 l.) was transferred to a separatory funnel and the layers separated. The aqueous phase was further extracted with 500 ml. of ether. The combined ether extract was washed with water (3×800 ml.) and dried over anhydrous $MgSO_4$. Evaporation of ether to dryness in a rotary evaporator yielded a crude material which on crystallization from ether-petroleum ether (30°–60° C.) (~1:30) resulted in 5-[4-methoxy-2,3,6-trimethylphenyl]-2(Z,E)-fluoro-3-methyl-2,4(E)-pentadien-1-ol as yellow crystals, m.p. 48°–80° C.

EXAMPLE 8

5-[4-methoxy-2,3,6-trimethylphenyl]-2-fluoro-3-methyl-2(Z),4(E)-pentadien-1-al and 5-[4-methoxy-2,3,6-trimethylphenyl]-2-fluoro-3-methyl-2(E),4(E)-pentadien-1-al 53.5 G. of 5-[4-methoxy-2,3,6-trimethylphenyl]-2(Z,E)-fluoro-3-methyl-2,4(E)-pentadien-1-ol was dissolved in 300 ml. of methylene chloride and added in several portions to a mechanically stirred mixture of manganese dioxide (200 g.) in 800 ml. of methylene chloride under argon. The mixture was stirred in dark for 3 days. More $MnO_2$ (100 g.) was added and stirring was continued under argon for four more days. The mixture was filtered through celite and the cake was washed well with methylene chloride (ca 1.5 l.). The solvent was evaporated to dryness in a rotary evaporator to yield a light brown colored oil which was chromatographed on 1.4 kg. of silica gel. Elution with diethyl ether-hexane (1:9) yielded a crystalline substance, which was recrystallized once from ether-petroleum ether (1:1) to yield pure 5-(4-methoxy-2,3,6-trimethylphenyl)-2-fluoro-3-methyl-2(E),4(E)-pentadien-1-al as light yellow crystals m.p. 79°–84° C. The column was further eluted with diethyl ether-hexane (1:4) to yield 5-(4-methoxy-2,3,6-trimethylphenyl)-2-fluoro-3-methyl-2(Z),4(E)-pentadien-1-al as light yellow crystals, m.p. 87°–91° C. An analytical sample had m.p. 89°–93° C. after recrystallization twice from ether.

EXAMPLE 9

9-(4-methoxy-2,3,6-trimethylphenyl)-6-fluoro-3,7-dimethyl-2(E),4(E),6(Z),8(E)-nonatetraenoic acid methyl ester 1.152 G. of sodium hydride (50% oil dispersion, 0.024 mol.) was placed into a 250.0 ml. three-necked flask and washed with 2×50 ml. of pentane. 25 Ml. of ethylene glycol dimethyl ether (distilled from lithium aluminum hydride) was added. 5.328 G. (0.024 mol) of methyl-4-dimethylphosphono-3-methylcrotonate in 25 ml. of ethylene glycol dimethyl ether was added dropwise to the above mixture, under argon, with mechanical stirring over a period of 20 min. The resulting mixture was further stirred under argon at 23° C. for 2.0 hrs. 6.288 G. (0.024 mol) of 5-[4-methoxy-2,3,6-trimethylphenyl]-2-fluoro-3-methyl-2(Z),4(E)-pentadien-1-al in 55 ml. of glyme was added dropwise over a period of 35 min. to the dark brown solution. A dark brown syrup appeared. The mixture was again stirred under argon at 23° C. for 2½ hrs. It was cooled in an ice-bath and ice-water (500 ml.) was added and the solution was neutralized with 1N HCl to pH 5–6. Methylene chloride (200 ml.) was added and stirring was continued for a few minutes. The layers were separated and the aqueous phase was further extracted with methylene chloride (3×200 ml.). The combined methylene chloride extract was washed with water (3×100 ml.) and dried over anhydrous $MgSO_4$. The solvent was removed in a rotary evaporator at 40° C./30 mm. to yield a crude product which was chromatographed on 300 g. of silica gel and elution with ether-petroleum ether (30°–60° C.) (1:9) to yield a yellow-orange crystalline substance. Fractional crystallizations of the yellow-orange crystalline substance from methylene chloride-petroleum ether (1:4) or acetone, yielded pure 9-(4-methoxy-2,3,6-trimethylphenyl)-6-fluoro-3,7-dimethyl-2(E),4(E),6(Z),8(E)-nonatetraenoic acid methyl ester, as yellow-orange crystals, m.p. 119°–121.5° C.

EXAMPLE 10

9-(4-methoxy-2,3,6-trimethylphenyl)-6-fluoro-3,7-dimethyl-2(Z),4(E),6(Z),8(E)-nonatetraenoic acid methyl ester The mother liquor from Example 9 was evaporated to dryness and the resulting oily residue was crystallized from ether-petroleum ether (ca 1:1) at 23° C. to yield 9-(4-methoxy-2,3,6-trimethylphenyl)-6-fluoro-3,7-dimethyl-2(Z),4(E), 6(Z),8(E)-nonatetraenoic acid methyl ester as yellow crystals, m.p. 134°–139.5° C.

EXAMPLE 11

9-(4-methoxy-2,3,6-trimethylphenyl)-6-fluoro-3-7-dimethyl-2(E),4(E),6(E),8(E)-nonatetraenoic acid methyl ester 5.32 G. (0.024 mol) of dimethyl-(2-methyl-3-carbomethoxy-2-propen-1-yl) phosphonate in 25 ml. of dry glyme was added dropwise to a suspension of sodium hydride (1.152 g., 0.024 mol, 50% dispersion) which has been washed with petroluem ether to remove the oil, in dry glyme (25 ml.). The resulting reaction mixture was stirred under argon at 25° C. for 1½ hrs. 6.288 G. (0.024 mol) of 5-(4-methoxy-2,3,6-trimethyl)-2-fluoro-3-methyl-2(E),4(E)-pentadien-1-al in 50 ml. of glyme was added dropwise. The resulting reaction mixture was then stirred at 25° C. for 17 hrs. and refluxed for 1.0 hr. under argon. It was then cooled in an ice-bath. Ice water (500 ml.) was added and the resulting solution was acidified with 1 N aqueous HCl to ca. pH 3–4. It was then extracted with $CH_2Cl_2$ (3×200 ml.). The combined methylene chloride extract was washed with water (3×100 ml.), dried over anhydrous $MgSO_4$ and concentrated in vacuo to yield an orange crystalline substance which was purified by chromatography on 200 g. of silica gel. Elution with 5–10% ether in petroleum ether yielded yellow crystals which upon recrystallization twice from $CH_2Cl_2$-petroleum ether (1:4) gave 9-(4-methoxy-2,3,6-trimethylpheny)-6-fluoro-3,7-dimethyl-2(E),4(E),6(E),8(E)-nonatetraenoic acid methyl ester, as yellow needles, m.p. 133°–141° C. An analytical sample was obtained by recrystallizing the above materials once more, m.p. 139°–143° C.

EXAMPLE 12

9-(4-methoxy-2,3,6-trimethylphenyl)-4-fluoro-3,7-dimethyl-2(E),4(E),6(E),8(E)-nonatetraenoic acid ethyl ester and
9-(4-methoxy-2,3,6-trimethylphenyl)-4-fluoro-3,7-dimethyl-2(E),4(Z),6(E),8(E)-nonatetraenoic acid ethyl ester 4.88 G. (0.0173 mol) of ethyl 4-diethylphosphono-4-fluoro-3-methyl-transcrotonate in 20 ml. of glyme was added dropwise, at 23° C. under argon to a suspension of 1.25 g (0.026 mol, 50% oil dispersion) of sodium hydride, which had been washed with petroleum ether to remove the oil, in 60 ml. of dry glyme (distilled from lithium aluminum hydride). The resulting mixture was stirred at 23° C. for 10 min. and then refluxed for 1¼ hrs. with stirring under argon. It was then cooled to 35° C.–40° C. over a period of one hour. 4.23 G. (0.0173 mol) of 5-(4-methoxy-2,3,6-trimethylphenyl)-3-methyl-2(E),4(E)-pentadien-1-al in 20 ml. of glyme over a period of ½ hr. was then added dropwise to the resulting light brown reaction mixture. The resulting reaction mixture was stirred at 23° C. for 1½ hrs. and then refluxed for 45 min. under argon. It was then cooled in an ice bath and ca 400 ml. of crushed ice-water was added. The resulting solution was then adjusted to pH ~2 with 1 N aqueous hydrochloric acid. Methylene chloride (250 ml.) was added and the resulting mixture was stirred for about 10 min. The aqueous phase was then separated from the methylene chloride phase and was further extracted with methylene chloride (3×150 ml.). The combined methylene chloride extracts were washed with water (2×100 ml.), dried over anhydrous magnesium sulfate, filtered, and evaporated in vacuo to give a brown oily product which was purified by column chromatography on silica gel (700 g.). Elution with 5% ether in petroleum ether yielded yellow crystalline 9-(4-methoxy-2,3,6-trimethylphenyl)-4-fluoro-3,7-dimethyl-2(E),4(E),6(E),8(E)-nonatetraenoic acid ethyl ester as the less polar isomer, m.p. 76°–83° C. which upon recrystallization from petroleum ether yielded the pure substance, m.p. 78°–84° C. The column was further eluted with 5–10% ether in petroleum ether to give the more polar isomer, m.p. 84°–93° C. which upon recrystallization from ether yielded pure 9-(4-methoxy-2,3,6-trimethylphenyl)-4-fluoro-3,7-dimethyl-2(E),4(Z),6(E),8(E)-nonatetraenoic acid ethyl ester as yellow crystals, m.p. 92.5°–96.5° C.

EXAMPLE 13

4-(4-methoxy-2,3,6-trimethylphenyl)-1,1,1-trifluoro-2-butyn-4-ol 43.4 G. (0.40 mol) of ethyl bromide was added dropwise over a period of 1 hr. under argon to a refluxing mixture of 10.6 g. (0.436 mol) of magnesium metal in 1.0-1. of dry ether. The resulting reaction mixture was further refluxed with stirring for 1½ hrs., and then cooled to 23° C. To this mixture of ethylmagnesium bromide, trifluoropropyne (41.0 g., 0.436 mol) was added through a gas dispersion tube. The resulting reaction mixture was stirred at 23° C. under argon while the trifluoropropyne was recycled 3 times. A brown colored viscous oil of trifluoropropynyl magnesium bromide was formed. 50 G. (0.281 mol) of 2,3,6-trimethyl-4-methoxy-benzaldehyde was added to this mixture, under argon, with vigorous stirring at 23° C. over a period of 30 min. It was further stirred at 23° C.–30° C. for 2 hrs. More 2,3,6-trimethyl-4-methoxy-benzaldehyde (10 g., 0.056 mol) in ether (100 ml.) was added and the reaction was further stirred for 1 hr. The mixture was cooled in an ice bath and a saturated aqueous solution of ammonium chloride was added slowly with stirring. The layers were separated and the aqueous phase was extracted three times with ether. The combined ether extract was washed with water and dried over anhydrous magnesium sulfate. Evaporation of the ether to dryness at reduced pressure gave a crude product which was recrystallized twice from chloroform-hexane to yield 4-(4-methoxy-2,3,6-trimethylphenyl)-1,1,1-trifluoro-2-butyn-4-ol as white crystals, m.p. 126°–130° C. An analytical sample had m.p. 127°–129.5° C.

EXAMPLE 14

4-(4-methoxy-2,3,6-trimethylphenyl)-1,1,1-trifluoro-3(E)-buten-2-one

92 Mg. (0.344 mmol) of mercuric sulfate and 0.05 ml. of concentrated sulfuric acid in 5 ml. of acetic acid was added to a solution of 277 mg. (1.02 mmol) of 4-(4-methoxy-2,3,6-trimethylphenyl)-1,1,1-trifluoro-2-butyn-4-ol in 10 ml. of glacial acetic acid. The resulting mixture was refluxed with stirring for 2 hrs. It was then diluted with 150 ml. of ice water and extracted with ether (3×40 ml.). The combined ether extract was washed with water and dried over anhydrous MgSO₄. Evaporation of solvent to dryness in vacuo (45°–50° C./20 mm) yielded a yellow crystalline substance which was recrystallized twice from petroleum ether to give 4-(4-methoxy-2,3,6-trimethylphenyl)-1,1,1-trifluoro-3(E)-buten-2-one as yellow crystals, m.p. 79°–82° C.

In a similar manner, this crystalline substance was prepared from 60 g. of 4-(4-methoxy-2,3,6-trimethylphenyl)-1,1,1-trifluoro-2-butyn-4-ol).

EXAMPLE 15

Methyl 5-(4-methoxy-2,3,6-trimethylphenyl)-3-trifluoromethyl-2(E),4(E)-pentadienoate 20.08 G. (0.111 mol) of trimethyl phosphono acetate in 50 ml. of glyme was added dropwise at 0° C. to a suspension of 4.92 g. (0.103 mol) sodium hydride (50% oil dispersion), which had been washed with pentane to remove the oil, in 200 ml. of glyme. The resulting mixture was stirred at 23° C. under argon for 2 hrs. 26 G. of 4-(4-methoxy-2,3,6-trimethylphenyl)-1,1,1-trifluoro-3(E)-buten-2-one in 200 ml. of glyme was then added dropwise to the resulting white paste-like mixture. The resulting reaction mixture was stirred at 23° C. for ½ hr. and then refluxed for 2 hrs. It was then cooled in an ice bath and the contents were poured into 1.0 l. of ice water. The resulting solution was neutralized to pH 7 with aqueous 2 N HCl and then extracted with $CH_2Cl_2$ (3×200 ml.). The combined methylene chloride extract was washed with water, brine and dried over anhydrous magnesium sulfate. Evaporation of methylene chloride solution to dryness in vacuo gave a crude product which was purified by column chromatography on silica gel (700 g.). Elution with 3% ether in petroleum ether yielded methyl 5-(4-methoxy-2,3,6-trimethylphenyl)-3-trifluoromethyl-2(E),4(E)-pentadienoate, which upon crystallization from pentane at −72° C. gave yellow crystals, m.p. 42°–48° C.

EXAMPLE 16

5-(4-methoxy-2,3,6-trimethylphenyl)-3-trifluoromethyl-2(E),4(E)-pentadien-1-ol 69.5 Ml. (0.106 mol) of diisobutylaluminum hydride (1.53 M in hexane) was added dropwise to a solution of 17.44 g. (0.0531 mol) of 5-(4-methoxy-2,3,6-trimethylphenyl)-3-trifluoromethyl-2(E),4(E)-pentadienoate in 500 ml. of dry ether, at 72° C. over a period of ½ hr. The resulting solution was stirred at −72° C. for 20 min. under argon. More diisobutylaluminum hydride (25 ml., 38.25 mmol) was added and the reaction mixture was further stirred for 30 min. at −72° C. To the resulting yellow solution was then added 100 ml. of methanol-water (1:1) at −72° C. with stirring. The resulting mixture was stirred and warmed to 23° C. slowly. The precipitate which forms was removed by filtration and washed well with ether. The ether phase of the filtrate was separated and washed with water, brine and dried (MgSO₄). Evaporation of the ether solution to dryness in vacuo yielded a yellow crude crystalline substance, which upon recrystallization from petroleum ether afforded 5-(4-methoxy-2,3,6-trimethylphenyl)-3-trifluoromethyl-2(E),4(E)-pentadien-1-ol, m.p. 69°–71° C.

EXAMPLE 17

5-(4-methoxy-2,3,6-trimethylphenyl)-3-trifluoromethyl-2(E),4(E)-pentadien-1-al

A mixture of MnO₂ (78 g., 0.896 mol) and 13 g. (0.0434 mol) of 5-(4-methoxy-2,3,6-trimethylphenyl)-3-trifluoromethyl-2(E),4(E)-pentadien-1-ol in dry methylene chloride (750 ml.) was stirred at 23° C. under argon for 15 hrs. The resulting mixture was filtered through celite and the precipitate was washed well with methylene chloride (total 1.0 l.). The methylene chloride was evaporated to dryness in vacuo to give an oily crude product which was purified by column chromatography on 600 g. of silica gel. Elution with 5% ether in petroleum ether gave 5-(4-methoxy-2,3,6-trimethylphenyl)-3-trifluoromethyl-2(E),4(E)-pentadien-1-al as a yellow oil. An analytical sample was obtained by crystallization from pentane, m.p. 55°–58° C. as yellow crystals.

EXAMPLE 18

9-(4-methoxy-2,3,6-trimethylphenyl)-3-methyl-7-trifluoromethyl-2(E),4(E),6(E),8(E)-nonatetraenoic acid methyl ester 745 Mg. (3.35 mmol) of dimethyl-(2-methyl-3-carbomethoxy-2-propen-1-yl) phosphonate in 5 ml. of glyme was added at 0° C. to a suspension of 116 mg. (3.35 mmol) of sodium hydride (50% oil dispersion, the oil was removed by washing three times with pentane) in dry glyme (5 ml.). The resulting mixture was first stirred at 0° C. for 10 min. and then at 23° C. for 1 hr. under argon. To the above mixture was then added 1.0 g. (3.35 mmol) of 5-(4-methoxy-2,3,6-trimethylphenyl)-3-trifluoromethyl-2(E),4(E)-pentadien-1-al in 5 ml. of glyme over a period of 15 min. The resulting reaction mixture was stirred at 23° C. for 3 hrs. and further refluxed for ½ hr. It was cooled in an ice bath and (250 ml.) of water was added. The solution was adjusted to pH 4 with aqueous 1 N HCl and then extracted with methylene chloride (4×50 ml.). The combined methylene chloride extracts were washed with water, brine and dried (MgSO₄). Evaporation of methylene chloride in vacuo yielded a crude product which was purified by column chromatography on 25 g. of silica gel. Elution with 5% ether in petroleum ether gave 5-(4-methoxy-2,3,6-trimethylphenyl)-3-trifluoromethyl-2(E),4(E)-pentadien-1-al. Further elution with 5% ether in petroleum ether afforded 9-(4-methoxy-2,3,6-trimethylphenyl)-3-methyl-7-trifluoromethyl-2(E),6(E),8(E)-nonatetraenoic acid methyl ester, as yellow crystals, m.p. 112°–113.5° C. upon recrystallization from petroleum ether.

EXAMPLE 19

Ethyl 7-(4-methoxy-2,3,6-trimethylphenyl)-2-fluoro-5-methyl-2(Z,E),4(E),6(E)-heptatrienoate 20.16 G (0.42 mol) of 50% sodium hydride was added to a 3 liter three-necked flask under argon and washed with three 50 ml. portions of pentane. The flask was then charged with 250 ml. of dry dimethoxyethane. 79.92 G (0.33 mol) of triethylphosphonofluoro acetate was added dropwise to the resulting mixture with stirring over a period of 0.5 hr. at 23° C. The reaction was furthere stirred and heated at 40° C. for 1.0 hr. under argon and then cooled to room temperature. To the resulting yellow-orange mixture 75 g. (0.306 mol) of 5-(4-methoxy-2,3,6-trimethylphenyl)-3-methyl-2(E),-4(E)-pentadien-1-al in 500 ml. of dry dimethoxyethane was added dropwise, with stirring under argon. The resulting reaction mixture was stirred at 23° C. for 2.0 hrs. and at 40° C. for aother 2.0 hrs. The resulting mixture was cooled to ~20° C. and poured onto 500 ml. of crushed ice-water then adjusted to pH ~4 by adding portions of 1.0 N HCl with stirring. The solution was extracted four times with 500 ml. of ether. The combined ether extracts were washed four times with 500 ml. of water, then 500 ml. of brine and dried over anhydrous MgSO₄. Evaporation of the ether to dryness at aspirator pressure yielded a dark orange oil which was quickly filtered through 2.2 kg. of silica gel. Elution with 10–20% by volume ether in petroleum ether (30°–60° C.) yielded an oily ester as mixture of isomers (E:Z ~3:2 by tlc). The column was further eluted with 40% ether to remove unreacted starting material. The resulting mixture of isomeric esters was used directly for conversion into ethyl 7-(4-methoxy-2,3,6-trimethylphenyl)-2-fluoro-5-methyl-2-(Z), 4(E),6(E)-heptadienoate.

EXAMPLE 20

Ethyl 7-(4-methoxy-2,3,6-trimethylphenyl)-2-fluoro-5-methyl-2(E),4(E),6(E)-heptatrienoate 66.1 G (0.199 mol) of 7-(4-methoxy-2,3,6-trimethylphenyl)-2-fluoro-5-methyl-2(Z,E),4(E),6(E)-heptatrienoate (E:Z ~3:2) was dissolved in 600 ml. of dry ether and 1.4 g. of crystalline iodine was added portionwise to the solution. The resulting soluton was stirred under argon at 23° C. for 48 hrs. and then washed three times with 200 ml. of 5% sodium thiosulfate solution, twice with 200 ml. of water and dried over anhydrous MgSO₄. Evaporation of most of the ether in a rotary evaporator at reduced pressure yielded a concentrated solution which was quickly passed through 100 g. of florisil. The column was washed with 1.5 l. of ether and the residue which was obtained after evaporation of the ether to dryness was then redissolved in 100 ml. of ether and diluted with 600 ml. of petroleum ether (30°–60° C.). This solution was kept at 23° C. for 1.0 hr. and at 0°

C. for 3.0 hrs. The resulting crystals were collected, washed with cold petroleum ether and dried to yield yellow crystals of 7-(4-methoxy-2,3,6-trimethylphenyl)-2-fluoro-5-methyl-2(Z),4(E),6(E)-heptatrienoic acid, ethyl ester, mp 106°–110° C. The mother liquor was evaporated to dryness to yield an oil which was dissolved in 750 ml. of ether. 0.83 G. of iodine crystals were added to the resulting solution which was then stirred under argon at 23° C. for 70 hrs. and worked up as above to yield yellow crystals of 7-(4-methoxy-2,3,6-trimethylphenyl)-2-fluoro-5-methyl-2(Z),4(E),6(E)-heptatrienoic acid ethyl ester, mp. 109°–111° C.

EXAMPLE 21

7-(4-methoxy-2,3,6-trimethylphenyl)-2-fluoro-5-methyl-2(Z),4(E),6(E)-heptatrienoic acid 150 Ml. of methanol and 40 ml. of 6 N sodium hydroxide were added to 41.5 g. (0.125 mol) of 7-(4-methoxy-2,3,6-trimethylphenyl)-2-fluoro-5-methyl-2(Z),4(E),6(E)-heptatrienoic acid, ethyl ester dissolved in 450 ml. of THF. The resulting solution was stirred at 23° C. for 15 minutes. A white precipitate was formed. 500 Ml. of water was added to dissolve the precipitate. The resulting solution was then stirred for 1.0 hr. at 23° C. and most of the THF and methanol were evaporated off at 50° C. at aspirator pressure. 150 Ml. of water was then added and the solution was extracted twice with 200 ml. of ether. The resulting alkaline aqueous phase was cooled to 0°–4° C. and acidified to pH ~3–4 with concentrated hydrochloric acid and then extracted three times with 300 ml. of ether. The combined ether extracts were washed twice with 200 ml. of water, once with 200 ml. of brine and dried over anhydrous $MgSO_4$.

The solvent was evaporated to dryness at reduced pressure to yield yellow crystals of 7-(4-methoxy-2,3,6-trimethylphenyl)-2-fluoro-5-methyl-2(Z),4(E), 6(E)-heptatrienoic acid, m.p. 203°–210°.

EXAMPLE 22

8-(4-methoxy-2,3,6-trimethylphenyl)-3-fluoro-6-methyl-3(Z),5(E),7(E)-octatrien-2-one 37.82 G. (0.124 mol) of 7-(4-methoxy-2,3,6-trimethylphenyl)-2-fluoro-5-methyl-2(Z),4(E),6(E)-heptadienoic acid which had been dried in a desiccator containing $P_2O_5$, at ~0.5 mm. for 24 hrs., were dissolved in 400 ml. of dry THF and cooled in a dry ice-acetone bath. 154 Ml. (0.248 mol) of methyl lithium (1.61 molar in ether) was added dropwise at −72° C. under argon from a syringe to the resulting solution with stirring. After the addition was completed, the reaction mixture was stirred at −75° C. under argon for 15 minutes. TLC (silica gel, EtOAc-hexane 3:7) indicated some acid still present. Another 15.4 ml. (0.025 mol) of methyl lithium was then added again in the same manner as before. The resulting reaction mixture was stirred at −75° C. for 1.0 hr. TLC showed some acid still present. However, no more methyl lithium was added since an excess of this reagent produced a tert-alcohol as the side product. The cold bath was removed and 150 ml. of water was carefully added. Most of the THF was removed at 50° C.- 30–50 mm. The aqueous solution was extracted three times with 300 ml. of ether. The combined ether extracts were washed three times with 300 ml. of water and dried over anhydrous $MgSO_4$. Evaporation of the ether to dryness at reduced pressure yielded a crude product which was dissolved in 50 ml. of methylene chloride and diluted with 300 ml. of hexane. The resulting solution was kept at 23° C. for 1.0 hr. and crystallization occurred. After further refrigeration for 18 hrs. the resulting crystals were collected, washed with 200 ml. of cold hexane and dried to yield orange crystals the product, 8-(4-methoxy-2,3,6-trimethylphenyl)-3-fluoro-6-methyl-3(Z),5(E),7(E)-octatrien-2-one, m.p. 108°–110° C. From the mother liquor there was obtained as a second crop orange crystals of the product, m.p. 107°–110° C.

EXAMPLE 23

9-(4-methoxy-2,3,6-trimethylphenyl)-4-fluoro-3,7-dimethyl-2(E),4(Z),6(E),8(E)-nonatetraenoic acid ethyl ester 2.37 G (0.0494 mol) of 50% sodium hydride oil dispersion were added to a flame dried 500 ml. three-necked flask under argon and then washed three times with 10 ml. of pentane to remove the oil. After addition of 10 ml. of dry dimethoxyethane (distilled from $NaAlH_2(OCH_2CH_2OCH_3)_2$) 11.08 g. (0.0494 mol) of triethylphosphono acetate in 30 ml. of dry dimethoxyethane were added dropwise, with stirring at 23° C. The reaction mixture was stirred at 23° C. until no more hydrogen was evolved (~1.0 hr). 10 G. (0.033 mol) of 8-(4-methoxy-2,3,6-trimethylphenyl)-3-fluoro-6-methyl-3(Z),5(E),7(E)-octatrien-2-one in 75 ml. of dimethoxymethane were then added dropwise at 23° C. to the resulting brown mixture, with stirring under argon. After the addition was completed the reaction mixture was stirred at 23° C. for 0.5 hr and then at 50° C. for 2.0 hr. under argon. TLC (silica gel EtOAc-hexane 15:85) showed no more starting material present. The reaction mixture was then cooled to ~20° C. and poured onto 200 ml. of cold water containing crushed ice. The resulting mixture was acidified to pH 4 by adding dropwise, with stirring concentratic hydrochloric acid. The reaction was then extracted three times with 200 ml. of ether. The combined ethereal extracts were washed three times with 200 ml. of water and dried over anhydrous $MgSO_4$. After evaporation of the ether to dryness the resulting crude product was quickly passed through 200 g. of florisil and eluted with 10% ether-petroleum ether. The eluant was collected, and concentrated almost to dryness at aspirator pressure at ~40° C. The resulting residue was added to 300 ml. of methylene chloride and treated with 10 g. of Norit A on a steam bath for ~2 min. then filtered and washed with 400 ml. of methylene chloride. A yellow crystalline material formed on evaporation of the methylene chloride to dryness at 35°–40°/20–30 mm. The crystalline material was dissolved in 25 ml. of ether containing 1 ml. of methylene chloride and further diluted with 50 ml. of petroleum ether (30°–60° C.) The resulting solution was kept at 23° C. for several hours and crystallization occurred. After further cooling at 0°–4° C. for 18 hrs., the crystals were collected, washed with 50 ml. of petroleum ether and dried to yield pure 9-(4-methoxy-2,3,6-trimethylphenyl)-4-fluoro-3,7-dimethyl-2-(E),4(Z),-6(E),8(E)-nonatetraenoic acid ethyl ester.

EXAMPLE 24

3-(4-methoxy-2,3,6-trimethylphenyl)-2-fluoro-2-(Z,E)-propenoic acid ethyl ester

60 G. (0.248 mol) of triethylphosphonofluoro acetate in 50 ml. of dimethoxyethane was added dropwise at 23° C., over a period of 2.0 hrs. to a suspension of 17.8 g. (0.37 mol) of 50% sodium hydride oil dispersion which had been washed with petroleum ether to remove the oil, in 150 ml. of dry dimethoxyethane. The resulting mixture was stirred at 23° C. for 3.0 hrs. When evolution of hydrogen was no longer observed, 2,3,6-trimethylanisaldehyde (44 g., 0.247 mol) in 50 ml. of dry dimethoxyethane was added over a period of 15 min. The mixture was stirred at 23° C. under argon for 20 hrs. Another 20 g. (0.0825 mol) of triethylphosphonofluoro acetate in 20 ml. of dimethoxyethane was then added in several portions. The reaction mixture was refluxed with stirring for 1.5 hrs. under argon. After the reaction mixture was cooled to ~30° C., 1.92 g. of 50% sodium hydride (0.04 mol) and 5.0 g. (0.0206 mol) of triethylphosphonofluoro acetate in 10 ml. of dimethoxyethane were added. After refluxing for another 0.5 hr., tlc indicated that the reaction did not proceed any further. The resulting reaction mixture was cooled to ~4° C. and poured onto 1.0 l. of crushed ice-water. The solution which formed was acidified to pH 2 by adding portionwise 150 ml. of 1 N HCl. The resulting solution was extracted three times with 400 ml. of methylene chloride. The combined methylene chloride extracts were washed five times with 500 ml. water once with 250 ml. brine and dried over anhydrous $Na_2SO_4$. Evaporation of the solvent to dryness at reduced pressure yielded a brown oily material, which was shown to contain approximately 90-95% product by tlc.

The oily material was purified by column chromatography on 1.50 kg. of silica gel. Elution with 1:19 to 1:9 ether-petroleum ether (30°-60° C.) yielded 3-[4-methoxy-2,3,6-trimethylphenyl]-2-fluoro-2-(Z,E)-propenoic acid ethyl ester as a light yellow oil.

EXAMPLE 25

3-(4-methoxy-2,3,6-trimethylphenyl)-2-fluoro-2-(Z,E)-propenoic acid 97.7 Ml. (0.586 mol) of aqueous 6 N NaOH was added dropwise to a stirred solution of 78.10 g. (0.293 mol) of 3-[4-methoxy-2,3,6-trimethylphenyl]-2-fluoro-2-(Z,E)-propenoic acid ethyl ester in 150 ml. of methanol. A white precipitate appeared and became very thick. The resulting mixture was stirred rapidly for 0.5 hr. at 23° C., and then diluted with 1.0 l. of ice-water. ~50 Ml. of concentrated hydrochloric acid was added dropwise to the well stirred mixture until it reached pH 1. The white solid which precipitated was extracted three times into 400 ml. ether. The combined ether extracts were washed once with 500 ml. brine and dried over anhydrous $Na_2SO_4$. Evaporation of the ether to dryness at reduced pressure yielded a white solid m.p. 157°-184°, which was dried over $P_2O_5$ in high vacuum at 23° C. for several days to yield 3-(4-methoxy-2,3,6-trimethyl)-2-fluoro-2(Z,E)-propenoic acid, m.p. 163°-181°.

EXAMPLE 26

4-(4-methoxy-2,3,6-trimethylphenyl)-3-fluoro-3(Z)-buten-2-one

A solution of 25 g. (0.105 mol) of 3-(4-methoxy-2,3,6-trimethylphenyl)-2-fluoro-2(Z,E)-propenoic acid in 35 ml. of dry THF and 215 ml. of anhydrous ether was cooled to −70° C. in a dry ice-acetone bath. 47.5 Ml. of methyl lithium (0.105 mol, 2.23 M in ether) was then injected slowly from a hypodermic syringe to this cooled solution, with stirring under argon at such a rate that the internal temperature was maintained at −60° to −70° C. The mixture was stirred under argon at −70° C. for 10 minutes. Another 47.5 ml. of methyl lithium was then injected into the solution in the same manner. The resulting solution was stirred at −70° C. under argon for 1.0 hr. An additional 5 ml. (0.0115 mol) of methyl lithium was added again as before and stirring was continued for 10 min. The resulting reaction mixture was then poured cautiously onto 500 ml. of crushed ice-water, acidified with concentrated hydrochloric acid to pH ~1.0 and extracted with ether. This was separated into neutral and acidic fractions to yield the crude product, 4-[4-methoxy-2,3,6-trimethylphenyl]-3-fluoro-3(Z)-buten-2-one as a light yellow oil and a small amount of unchanged starting material as a white solid. The crude product was then purified by column chromatography on 1.6 kg. of silica gel (8.6×86 cm. column). Elution with 1:9 ether-petroleum ether yielded a low melting crystalline substance. Upon further elution with 1:9 ether-petroleum ether a crystalline E-isomeric ketone compound, m.p. 56°-59° C. was isolated. Further elution with the same eluant yielded the Z-isomer which was crystallized from petroleum ether (30°-60° C.) to yield 4-(4-methoxy-2,3,6-trimethylphenyl)-3-fluoro-3(Z)-buten-2-one, m.p. 34°-43.5° C.

EXAMPLE 27

5-[4-methoxy-2,3,6-trimethylphenyl]-3-methyl-4-fluoro-2(E),4(Z)-pentadienoic acid ethyl ester 26.84 G. (0.12 mol) of triethylphosphono acetate was added dropwise over a period of 25 minutes to a suspension of 5.75 g. (0.12 mol) of 50% sodium hydride oil dispersion, which had been washed with petroleum ether to remove the oil, in 200 ml. of dry dimethoxyethane. The mixture was stirred at 23° C. for 1.0 hr. then 23.53 g. (0.0997 mol) of unsaturated 4-[4-methoxy-2,3,6-trimethylphenyl]-3-fluoro-3(Z)-buten-2-one in 100 ml. of dimethoxyethane was added dropwise. The reaction mixture was stirred at 23° C. under argon for 1.25 hrs. Crushed ice-water (~1.0 l.) was slowly added and the solution was acidified to pH 2 with 6 N HCl. It was extracted with ether and worked up in the usual manner to yield a brown oily crude product which was purified by column chromatography on 600 g. of silica gel. Elution with 1:19 to 1:9 ether-petroleum ether (30°-60° C.) yielded a white crystalline powder, (5-(4-methoxy-2,3,6-trimethylphenyl)-3-methyl-4-fluoro-2(E),4(Z)-pentadienoic acid ethyl ester, m.p. 50°-51° C.

EXAMPLE 28

5-(4-methoxy-2,3,6-trimethylphenyl)-3-methyl-4-fluoro-2(E),4(Z)-pentadien-1-ol 86.5 Ml. (0.13 mol) of diisobutylaluminum hydride (1.5 M in hexane) was added dropwise to a solution of 19.48 g. (0.065 mol) of 5-(4-methoxy-2,3,6-trimethylphenyl)-3-methyl-4-fluoro-2(E),4(Z)-pentadienoic acid ethyl ester dissolved in 400 ml. of anhydrous ether and cooled to −65° C. under argon. The resulting mixture was stirred under argon at −65° C. for 5 minutes. More diisobutylaluminum hydride (17 ml., 0.0255 mol) was added again in two portions. The reaction mixture was stirred at −65° C. for approximately 20 minutes and the excess of hydride was destroyed by adding dropwise 85 ml. of 1:1 methanol-water at such a rate that the internal temperature did not exceed −30° C. 100 Ml. of water was then added and the mixture was stirred at ~10° C. for approximately 40 minutes. The precipitate which formed was filtered off and washed well with ether. The resulting layers were separated and the aqueous phase was further extracted with ether. The combined ether phases were washed with water, brine, and dried over anhydrous Na₂SO₄. Evaporation of the ether to dryness at reduced pressure yielded a crude product which was dissolved in 215 ml. of ether, diluted with 60 ml. of petroleum ether (30°–60° C.) and kept at −10° C. for 20 hrs. The crystals which formed were collected, washed with 50 ml. of petroleum ether and dried to yield pure 5-(4-methoxy-2,3,6-trimethylphenyl)-3-methyl-4-fluoro-2(E),4(Z)-pentadien-1-ol as pale yellow crystals, m.p. 71°–73.5°.

EXAMPLE 29

5-(4-methoxy-2,3,6-trimethylphenyl)-3-methyl-4-fluoro-2(E),4(Z)-pentadienal 13.84 g. (0.0524 mol) of 5-(4-methoxy-2,3,6-trimethylphenyl)-3-methyl-4-fluoro-2(E),4(Z)-pentadien-1-ol in 55 ml. of methylene chloride was added to a stirred mixture of manganese dioxide (54.66 g., 0.629 mol) in 60 ml. of methylene chloride. The resulting mixture was stirred in the dark, under argon for 65 hrs. and worked up as usual to yield a yellow crystalline substance which was recrystallized from ~1:4 methylene chloride-petroleum ether to yield 5-(4-methoxy-2,3,6-trimethylphenyl)-3-methyl-4-fluoro-2(E),4(Z)-pentadienal as yellow crystals, m.p. 85°–88.5° C. A sample was recrystallized once more for analysis and had a m.p. 86.5°–88.5° C.

EXAMPLE 30

9-(4-methoxy-2,3,6-trimethylphenyl)-8-fluoro-3,7-dimethyl-2(E),4(E),6(E),8(Z)-nonatetraenoic acid methyl ester 1.31 G. (0.027 mol) of 50% sodium hydride oil dispersion was placed in a dry flask and washed with 40 ml. of petroleum ether under argon. The petroleum ether was replaced by 60 ml. of dry dimethoxy-ethane. 6.06 G. (0.027 mol) of dimethyl-2-methyl-3-carbomethoxy-2-propen-1-yl) phosphonate in 30 ml. of dimethoxyethane was then added dropwise with stirring to the resulting slurry. The mixture was stirred at 23° C. until evolution of hydrogen stopped. 6.0 G. (0.0229 mol) of 5-(4-methoxy-2,3,5-trimethylphenyl)-3-methyl-4-fluoro-2(E),4(Z)-pentadienal in 30 ml. of dimethoxyethane was then added over a period of 10 minutes to the resulting dark brown mixture. The resulting reaction mixture was stirred at 23° C. under argon for 1.6 hrs. Crushed ice-water (~500 ml). was then slowly added. The solution was adjusted to pH ~1 with 6 N HCl and then immediately extracted with ether. It was then worked up in the usual manner to yield a crude product which was purified by column chromatography on silica gel (500 g., 4.5 cm × 84 cm column). Elution with 1:9 ether-petroleum ether yielded a yellow crystalline substance, containing mainly two isomers. This yellow crystalline substance was crystallized from methylene chloride-ether (1:3) to yield 9-(4-methoxy-2,3,6-trimethylphenyl)-8-fluoro-3,7-dimethyl-2(E),4(E),6(E),8(Z)-nonatetraenoic acid methyl ester as yellow crystals, m.p. 121.5°–130° C.

EXAMPLE 31

4-(diethoxyphosphinyl)-2(Z,E)-3-(trifluoromethyl)-crotonic acid ethyl ester

Ethyl-3-trifluoromethyl-4-bromo-2(Z,E)-butenoate (18.48 g., 70.7 mmol) and 12.95 g. (78 mmol) of triethylphosphite were heated at 140° C. for 3.0 hrs. while the ethyl bromide formed during the reaction was distilled off. The resulting crude product was distilled using a Vigreux column at 1 mm. to yield a colorless liquid, b.p. 105°–110° C. containing a 1:1 mixture of isomers including 4-diethoxyphosphinyl)-2(Z,E)-3-(trifluoromethyl)-crotonic acid ethyl ester and a bp 110°–113° C. mixture of the same isomers.

EXAMPLE 32

9-(4-methoxy-2,3,6-trimethylphenyl)-3-trifluoromethyl-7-methyl-2(E),4(E),6(E),8(E)-nonatetraenoic acid ethyl ester 9.44 G. (29.7 mmol) of 4-(diethoxyphosphinyl)-2(Z,E)-3-(trifluoromethyl)crotonic acid ethyl ester in 50 ml. of dimethoxyethane was added dropwise to a suspension of 1.42 g. (29.7 mmol) of 50% sodium hydride oil dispersion (the oil was removed by washing with pentane) in 25 ml. of dimethoxyethane, at 0° C. The resulting mixture was stirred at 23° C. until no more hydrogen gas was evolved (approximately one hr.). 6.59 G. (27 mmol) of 5-(4-methoxy-2,3,6-trimethylphenyl)-3-methyl-2(E),4(E)-pentadien-1-al in 50 ml. of dimethoxyethane was added dropwise to the resulting brown mixture, under argon. The resulting reaction mixture was stirred at 23° C. under argon for 5.0 hrs. and then poured onto crushed ice-water and adjusted to pH 3 with 2 N HCl and then extracted three times with 250 ml. ether. The combined ether extracts were washed with water and dried over anhydrous MgSO₄. Evaporation of the ether to dryness in vacuo yielded a brown oily material which was purified by column chromatography on 300 g. of silica gel. Elution with 1:19 ether-petroleum ether yielded of a crystalline substance which was further recrystallized from petroleum ether to yield pure 9-(4-methoxy-2,3,6-trimethylphenyl)-3-trifluoromethyl-2(E),4(E),6(E),8(E)-nonatetraenoic acid ethyl ester as bright yellow crystals, m.p. 72°–75° C.

EXAMPLE 33

Ethyl 2-fluoro-4-methyl-6-acetoxy-2(Z,E),4(E)-hexadienoate

70 G. (0.289 mol) of triethylphosphonofluoro acetate in 50 ml. of dimethoxyethane was added with stirring to a suspension of 14.28 g. (0.298 mol) of 50% sodium hydride oil dispersion (the oil was removed by washing with pentane) in 50 ml. of dry dimethoxyethane, under argon over a period of thirty minutes. The resulting mixture was stirred at 23° C. under argon until the evolution of hydrogen gas stopped. 39.8 G. (0.28 mol) of acetoxy tiglic aldehyde in 60 ml. of dimethoxyethane was added over a period of twenty-five minutes to the resulting mixture. The reaction mixture was stirred at 23° C. for 17 hrs. and diluted with ice-water (500 ml.). The resulting solution was acidified to pH 2 with 1 N HCl, and then extracted four times with 200 ml. ether. The combined ether extracts were washed with water and dried over anhydrous Na₂SO₄. The ether was evaporated to dryness at 35° C./150–180 mm. to yield a brown-colored liquid, which was purified by vacuum distillation at 0.45–0.50 mm. to yield a product containing mostly acetoxy tiglic aldehyde, b.p. 60° C. and ethyl 2-fluoro-4-methyl-6-acetoxy-2(Z,E),4(E)-hexadienoate as a light yellow liquid, b.p. 110°–115°. A sample was further purified, first by passing through a column of silica gel (14 g., elution with 1:9 to 1:4 ether-petroleum ether) and then evaporatively distilling to yield a colorless liquid, b.p. 124° C./0.6 mm.

EXAMPLE 34

Ethyl 2-fluoro-4-methyl-6-oxo-2(Z,E),4(E)-hexadienoate

A mixture of 24.8 g. of ethyl 2-fluoro-4-methyl-6-hydroxy-2(Z,E),4(E)-hexadienoate and 150 g. of manganese dioxide in 500 ml. of methylene chloride was stirred at 23° C., under argon for 3 days. The manganese dioxide was filtered over Celite and washed well with methylene chloride. The solvent was evaporated at 37° C./50 mm. to yield ethyl 2-fluoro-4-methyl-6-oxo-2(Z,E),4(E)-hexadienoate as a light yellow liquid, mass spectrum m/e 186 (M+).

EXAMPLE 35

Ethyl 2-fluoro-4-methyl-6,6-dimethoxy-2(Z,E),4(E)-hexadienate

A mixture of 19 g. of ethyl 2-fluoro-4-methyl-6-oxo-2(Z,E),4(E)-hexadienoate and 0.10 g. of ammonium chloride in 100 ml. of methanol was stirred at 23° C. under argon for 18 hours. The solution was then adjusted to pH ~8 by adding solid sodium bicarbonate. The reaction mixture was then filtered and the methanol was evaporated at 35° C./25-35 mm. to yield ethyl 2-fluoro-4-methyl-6,6-dimethoxy-2(Z,E),4(E)-hexadienoate as a light yellow liquid.

EXAMPLE 36

2-fluoro-4-methyl-6,6-dimethoxy-2(Z,E)4,(E)-hexadienal

A solution of 16 g. of ethyl 2-fluoro-4-methyl-6,6-dimethoxy-2(Z,E),4(E)-hexadienoate in 450 ml. of absolute ether was treated dropwise, over a period of 2.5 hours with 105 ml. of diisobutylaluminum hydride (~1.5 M in hexane) at −72° C., with stirring under argon. TLC showed no more starting material present. A mixture of 1:1 methanol-water (160 ml.) was then added slowly, followed by 90 ml. of cold water. The cooling bath was removed and the mixture was stirred at −50° C. to −5° C. over a period of 2.0 hours under argon. The precipitate which formed was removed by filtration and washed well with ether. The aqueous phase of the filtrate was separated and further extracted with ether. The combined ether phase was washed with water and dried over anhydrous magnesium sulfate. Evaporation of the ether at 35° C./30-40 mm. Under nitrogen gave a light yellow oil containing mainly the 2-fluoro-4-methyl-6,6-dimethoxy-2(Z,E),4(E)-hexadienal and approximately 10-20% of 2-fluoro-4-methyl-6,6-dimethoxy-2(Z,E),4(E)-hexadienol. The light yellow oil was dissolved in 150 ml. of methylene chloride and treated with 10 g. of activated manganese dioxide at 23° C. for 4.0 hours with stirring under argon. The resulting reaction mixture was filtered through Celite and washed with 100 ml. of methylene chloride. The methylene chloride filtrate (~300 ml.) containing the 2-fluoro-4-methyl-6,6-dimethoxy-2(Z,E),4(E)-hexadienal was kept under argon and was used directly for conversion into 9-(4-methoxy-2,3,6-trimethylphenyl)-3,7-dimethyl-5-fluoro-2(E),4(Z),6(Z,E),8(E)-nonatetraenal.

EXAMPLE 37

9-(4-methoxy-2,3,6-trimethylphenyl)-3,7-dimethyl-5-fluoro-2(E),4(Z),6(Z,E),8(E)-nonatetraenal A solution of 18 11 g. of 2-fluoro-4-methyl-6,6-dimethoxy-2(Z,E),4(E)-hexadienal in 300 ml. of methylene chloride was cooled to 4° C. and stirred under argon. To this solution, a suspension of 30 g. of 4(4-methoxy-2,3,6-trimethylphenyl)-3-buten-2-yltriphenylphosphonium chloride in 200 ml. of water was added in several portions. The mixture was again cooled to ~4° C. and a solution of 22 ml. of 6 N aqueous sodium hydroxide was added dropwise over a 5 minute period. The resulting mixture was stirred at 4° C. under argon for 40 minutes. It was then poured onto ~500 ml. of cold water and the layers were separated. The aqueous phase was further extracted with methylene chloride. The combined methyl chloride extracts were shaken two times with aqueous 2 N hydrochloric acid, washed with water and dried over anhydrous magnesium sulfate. Evaporation of methylene chloride to dryness at reduced pressure yielded a dark brown oily material. This crude product was purified by column chromatography on 850 g. of silica gel. Elution with ether-petroleum ether (3:7) yielded 9-(4-methoxy-2,3,6-trimethylphenyl)-3,7-dimethyl-5-fluoro-2(E),4(Z),6(Z,E),-8(E)-nonatetraenal as orange crystals, mp. 85°–115° C.

EXAMPLE 38

Methyl 9-(4-methoxy-2,3,6-trimethylphenyl)-3,7-dimethyl-5-fluoro-2(E),4(Z),6(Z,E),8(E)-nonatetraenoate To a solution of 2.44 g. of 9-(4-methoxy-2,3,6-trimethylphenyl)-3,7-dimethyl-5-fluoro-2(E),4(Z),6(Z,E),-8(E)-nonatetraenal in 20 ml. of methylene chloride and 150 ml. of methanol was added 1.47 g. of sodium cyanide, 7.8 g. of activated manganese dioxide and 650 mg. of glacial acetic acid. The resulting mixture was stirred at 23° C. for 18 hours under argon. The manganese dioxide was filtered on Celite and washed with ~500 ml. of methylene chloride and finally with 50 ml. of 1:1 methylene chloride-methanol. The combined filtrate was evaporated at reduced pressure and the residue was treated with ~500 ml. of water and ~100 ml. of methylene chloride. The aqueous phase was separated and extracted four times with methylene chloride. The combined methylene chloride phase was washed with water and dried over magnesium sulfate. Evaporation of methylene chloride at reduced pressure gave a brown oily substance. This crude material was purified by column chromatography on 150 g. of silica gel. Elution with ether-petroleum ether (1:4) yielded methyl 9-(4-methoxy-2,3,6-trimethylphenyl)-3,7-dimethyl-5-fluoro-2(E),4(Z),6(Z,E),8(E)-nonatetraenoate which crystallized from petroleum ether as yellow crystals, mp. 55°–80° C., (6Z:6E~5:2).

EXAMPLE 39

Diethyl-methoxy-2,3,6-trimethyl-benzylphosphonate

A mixture of 18 g. (0.074 mol.) of 4-methoxy-2,3,6-trimethyl benzyl bromide and 15.75 g. (0.095 mol.) of triethylphosphite was heated very carefully to 40°–50° C., at which point the reaction started vigorously. Heating should be discontinued, if necessary. After the vigorous reaction subsided, the mixture was heated again slowly to 150° C. and held at that temperature for two hours longer. The low boiling bromoethane was collected in a Dean Stark trap during the heting period.

The resulting mixture was then distilled at 0.15 mm. to give diethyl 4-methoxy-2,3,6-trimethyl benzylphosphate, bp. 140°-144° C./0.15 mm.

EXAMPLE 40

Ethyl 2(E),4(E),6(E),8(E)- and 2(E),4(E),6(E),8(Z)-dimethyl-9-fluoro-9-(4-methoxy-2,3,6-trimethylphenyl)-nonatetraenoate 3 Ml. (6.5 mmole) of 2.1 M of n-butyl lithium in hexane was added to a cold (−70° C.) solution of 2.16 g. (7.2 mmole) of diethyl 4-methoxy-2,3,6-trimethylbenzylphosphonate in 26 ml. of anhydrous tetrahydrofuran. The resulting pale yellow solution was allowed to warm to −27° C. in an ice-methanol bath and a mixture of argon and perchlorylfluoride was bubbled through the solution for 3-5 minutes. Then the perchlorylfluoride stream was discontinued and argon was continued for 15-20 minutes longer. A solution of 1.5 g. (7.2 mmole) of all trans-3-methyl-7-formyl-2,4,6-octatrienoic acid ethyl ester in 6 ml. of tetrahydrofuran was mixed well with the fluorinated phosphonate and the mixture was added dropwise to a cold (−70° C.) solution of lithium diisopropylamide, prepared by adding 3 ml. (6.5 mmol) of 2.1 M of n-butyl lithium in hexane to a cold (−65° C.) solution of 1.2 ml. (8.5 mmole) of diisopropylamine in 2 ml. of anhydrous tetrahydrofuran, over a 45 minute period. After the addition was complete, the resulting solution was stirred at −70° C. for 10 minutes longer and then poured onto a mixture of sodium chloride solution and ether. The organic layer was washed with sodium chloride solution until neutral and dried. Evaporation of the solvent gave a yellow oil.

The product from several preparations described above in this Example was combined (20 g.) and purified by chromatography on silica gel packed in hexane containing 5% ether. Elution with this solvent mixture gave a yellow solid which was treated with 2-3 ml. of pentane and filtered to give pure ethyl (2E,4E,6E,8Z)-3,7-dimethyl-9-fluoro-9-(4-methoxy-2,3,6-trimethylphenyl) nonatetraenoate, as pale yellow crystals, m.p. 120°-130° C.

The mother liquor from the above crystallization was cooled to −78° C. and filtered to give ethyl (2E,4E,6E,-8E)-3,7-dimethyl-9-fluoro-9-(4-methoxy-2,3,6-trimethylphenyl)-nonatetraenoate, as yellow crystals, m.p. 74°-87° C.

EXAMPLE 41

9-(4-methoxy-2,3,6-trimethylphenyl)-3,7-dimethyl-6-fluoro-2(E),4(E),6(Z),8(E)-nonatetraenal A solution of 500 mg. (1.39 mmol) of methyl 9-(4-methoxy-2,3,6-trimethylphenyl)-3,7-dimethyl-6-fluoro-2(E),4(E),6(Z),8(E)-nonatetraenoate in 20 ml. of absolute ether and under a stream of argon was cooled to −72° C. To this cooled solution, 3.72 ml. (5.56 mmol) of diisobutylaluminum hydride (1.5 M in hexane) was added dropwise at −72° C. with stirring under argon. The reaction was followed by TLC which showed no more starting material present. Methanol-water (1:1) was then added to the reaction mixture. Stirring was continued at 25° C. for 1.5 hours. The precipitate formed was removed by filtration and washed with ether. The ether phase of the filtrate was washed with water, dried over anhydrous magnesium sulfate and concentrated to give 9-(4-methoxy-2,3,6-trimethylphenyl)-3,7-dimethyl-6-fluoro-2(E),4(E),6(Z),8(E)-nonatetraenol as an orange oil. This material was dissolved in 40 ml. of methylene chloride and was stirred with 1.5 g. of activated manganese dioxide at 25° C. under argon for 20 hours. The reaction mixture was filtered through Celite and washed well with methylene chloride. Evaporation of the methylene chloride on a rotary evaporator yielded 9-(4-methoxy-2,3,6-trimethylphenyl)-3,7-dimethyl-6-fluoro-2(E),4(E),6(Z),8(E)-nonatetraenal as orange crystals, mp. 132°-136° C.

EXAMPLE 42

9-(4-methoxy-2,3,6-trimethylphenyl)-3,7-dimethyl-6-fluoro-2(E),4(E),6(E),8(E)-nonatetraenal The compound, mp. 133°-137° C., as yellow crystals, was prepared from methyl 9-(4-methoxy-2,3,6-trimethylphenyl)-3,7-dimethyl-6-fluoro-2(E),4(E),6(E),8(E)-nonatetraenate using the procedures described above for 9-(4-methoxy-2,3,6-trimethylphenyl)-3,7-dimethyl-6-fluoro-2(E),4(E),6(Z),8(E)-nonatetraenal.

EXAMPLE 43

9-(4-methoxy-2,3,6-trimethylphenyl)-3,7-dimethyl-4-fluoro-2(E),4(Z),6(E),8(E)-nonatetraenoic acid A mixture of 5.0 g. (13.4 mmol) of ethyl 9-(4-methoxy-2,3,6-trimethylphenyl)-3,7-dimethyl-4-fluoro-2(E),4(Z),6(E),8(E)-nonatetraenoate and 5.3 ml. (31.8 mmol) of 6 N aqueous sodium hydroxide in 25 ml. of tetrahydrofuran and 20 ml. of methanol-water (1:1) was heated at 80° C. for 4.0 hours. The resulting solution was concentrated on a rotary evaporator, diluted with water and washed with ether. The aqueous phase was acidified with concentrated hydrochloric acid, then extracted well with methylene chloride. The methylene chloride extracts were combined and concentrated to give the crude acid, which was dried over phosphorus pentoxide at 25° C., 0.5 mm. for 20 hours to yield yellow crystals. Recrystallization of this material from tetrahydrofuran-petroleum ether gave 9-(4-methoxy-2,3,6-trimethylphenyl)-3,7-dimethyl-4-fluoro-2(E),4(Z),-6(E),8(E)-nonatetraenoic acid as yellow crystals, mp. 254°-257° C.

EXAMPLE 44

9-(4-methoxy-2,3,6-trimethylphenyl)-3,7-dimethyl-4-fluoro-2(E),4(E),6(E),8(E)-nonatetraenoic acid ethyl amide Ethyl amine (∼3 ml.) was bubbled into a suspension of 900 mg. (2.62 mmol) of 9-(4-methoxy-2,3,6-trimethylphenyl)-3,7-dimethyl-4-fluoro-2(E),4(Z),6(E),8(E)-nonatetraenoic acid, 1.29 g. (6.9 mmol) of t-butylamine and 992 mg. (3.5 mmol) of 1-methyl-2-bromopyridinium iodide in 40 ml. of methylene chloride. The resulting mixture was stirred at 25° C. for 2 hours and further heated at 40° C. for 1.0 hour. It was then taken into methylene chloride, washed with water and dried over anhydrous magnesium sulfate. Concentration of methylene chloride on a rotary evaporator yielded yellow crystals which were chromatographed on 125 g. of silica gel. Elution with methanolchloroform (3:7) gave 9-(4-methoxy-2,3,6-trimethylphenyl)-3,7-dimethyl-4-fluoro-2(E),4(Z),6(E),8(E)-nonatetraenoic acid ethyl amide as yellow crystals, mp. 167°-169° C. (recrystallized from methylene chloride-hexane).

EXAMPLE 45

Ethyl 2(E,Z),4(Z),6(E),8(E)-2,4-difluoro-3,7-dimethyl-9-(4-methoxy-2,3,6-trimethylphenyl)nonatetraenoate A solution of 2.39 g. (9.9 mmol) of triethylphosphonofluoroacetate in 10 ml. of dry dimethoxyethane was added dropwise, at 23° C., under argon, a stirred suspension of 470 mg. (9.8 mmol) of sodium hydride (50% in oil dispersion, the oil was removed by washing with petroleum ether) in 2 ml. of dry dimethoxyethane. The mixture was stirred at 23° C. under argon for 2.0 hours. To the resulting yellow orange suspension was then added dropwise 1.0 g. (3.31 mmol) of 3(Z),5(E),-7(E)-3-fluoro-6-methyl-8-(4-methoxy-2,3,6-trimethylphenyl)-octatrien-2-one in 10 ml. of dimethoxyethane. The reaction mixture was stirred at 23° C. under argon for 15 minutes and then poured onto 100 ml. of ice/water. The resulting solution was adjusted to pH 4 with concentrated hydrochloric acid and then extracted four times with ether. The combined ether extracts were washed with water, dried over anhydrous magnesium sulfate and concentrated in vacuo to give 3.31 g. of yellow oily product. This material was filtered through 40 g. of florisil. Elution with methylene chloride yielded a material which on crystallization from hexane gave ethyl 2(E,Z),4(Z),6(E),8(E)-2,4-difluoro-3,7-dimethyl-9-(4-methoxy-2,3,6-trimethylphenyl)-nonatetraenoate as yellow crystals, mp. 59°–64° C.

EXAMPLE 46

Ethyl 2(Z),4(E),6(Z),8(E)-2,6-difluoro-3,7-dimethyl-9-(4-methoxy-2,3,6-trimethylphenyl)nonatetraenoate A solution of 12.4 g. (0.044 mol) of ethyl 2(Z,E)-2-fluoro-3-methyl-4-diethoxyphosphinylcrotonate in 10 ml. of dimethoxyethane was added dropwise, with stirring at 0° C., under argon, to a suspension of 2.1 g. (0.044 mol) of sodium hydride (50% in oil dispersion, the oil was removed by washing with petroleum ether) in 30 ml. of dimethoxyethane. The mixture was stirred under argon for 2.0 hours. To the resulting brown-colored suspension, a sample of 7.0 g. (0.027 mol) of 2(Z),4(E)-2-fluoro-3-methyl-5-(4-methoxy-2,3,6-trimethylphenyl)-pentadienal in 25 ml. of dimethoxyethane was slowly added. The resulting reaction mixture was stirred under argon for 18 hours and then was poured onto ice-water. The resulting aqueous solution was adjusted to pH~4 with 2 N hydrochloric acid and was then extracted with methylene chloride. The methylene chloride extracts were combined, washed with brine, dried over anhydrous magnesium sulfate, filtered and concentrated at reduced pressure to give an oily crude product. This crude material was filtered through a short column of silica gel. Elution with methylene chloride yielded ethyl 2(Z,E),4(E),6(Z),8(E)-2,6-difluoro-3,7-dimethyl-9-(4-methoxy-2,3,6-trimethylphenyl)-nonatetraenoate, which on two recrystallizations from ether-petroleum ether (~1:9) gave ethyl 2(Z),4(E),6(Z),8(E)-2,6-difluoro-3,7-dimethyl-9-(4-methoxy-2,3,6-trimethylphenyl)-nonatetraenoate as yellow crystals, mp. 134°–136° C.

EXAMPLE 47

Ethyl 2(Z),4(Z),6(E)-2,4-difluoro-5-methyl-7-(4-methoxy-2,3,6-trimethylphenyl)-heptatrienoate A 2.35 g. (0.049 mol) sample of 50% sodium hydride dispersion in oil was placed into a flask and washed under argon with petroleum ether to remove the oil. Dry dimethoxyethane (40 ml.) was then added and the mixture was cooled to an ice bath. To this suspension, a solution of 15.43 g. (0.063 mol) of triethyl phosphonofluoroacetate in 30 ml. of dimethoxyethane was added dropwise with stirring under argon. After the addition was complete, the ice bath was removed and the mixture was further stirred at 23° C. for about an hour. To the resulting golden yellow suspension, a solution of 12.83 g. (0.049 mol) of 2(Z),4(E)-2-fluoro-3-methyl-5-(4-methoxy-2,3,6-trimethylphenyl)pentadienal in 60 ml. of dimethoxyethane was added dropwise over a period of 30 minutes with vigorous stirring. The reaction mixture was stirred at 23° C. for 3.0 hours and further refluxed for 1.0 hour. It was then cooled in an ice bath and 400 ml. of ice-water was added. The resulting solution was adjusted to pH~4 with 4 N hydrochloric acid and extracted with methylene chloride. The combined organic extracts were processed in the usual manner to give 26 g. of crude product. This crude material was filtered through a short column of florisil. Elution with methylene chloride gave 2(Z,E),4(Z),6(E)-2,4-difluoro-5-methyl-7-(4-methoxy-2,3,6-trimethylphenyl)-heptatrienoate as a yellow solid, which on crystallization from ether-petroleum ether (1:4) yielded 2(Z),4(Z),6(E)-2,4-difluoro-5-methyl-7-(4-methoxy-2,3,6-trimethylphenyl)-heptatrienoate as yellow crystals, mp. 122°–125° C. The mother liquid from the above crystallization was concentrated and dissolved in ether. The resulting solution was treated with 235 mg. of crystalline iodine under argon in the dark, at 23° C. for 30 minutes and crystallization occurred. This was filtered to give 2(Z),4(Z),6(E)-2,4-difluoro-5-methyl-7-(4-methoxy-2,3,6-trimethylphenyl)-heptatrienoate as yellow crystals, mp. 122°–125° C.

EXAMPLE 48

2(Z),4(Z),6(E)-2,4-difluoro-5-methyl-7-(4-methoxy-2,3,6-trimethylphenyl)-heptatrienoic acid A mixture of 7.0 g. (0.02 mol) of ethyl 2(Z),4(Z),6(E)-2,4-difluoro-5-methyl-7-(4-methoxy-2,3,6-trimethylphenyl)-heptatrienoate and 5.5 ml. of 6 N aqueous sodium hydroxide in 400 ml. of methanol-tetrahydrofuran (1:1) was stirred at 23° C. under argon for 18 hours. The reaction mixture was poured into approximately 300 ml. of ice water and acidified with concentrated hydrochloric acid. Workup with methylene chloride in the usual manner gave 2(Z),4(Z),6(E)-2,4-difluoro-5-methyl-7-(4-methoxy-2,3,6-trimethylphenyl)-heptatrienoic acid as yellow crystals, mp. 209°–214° C.

EXAMPLE 49

3(Z),5(Z),7(E)-3,5-difluoro-6-methyl-8-(4-methoxy-2,3,6-trimethylphenyl)-octatrien-2-one A sample of 3.32 g. (0.0103 mol) of 2(Z),4(Z),6(E),-2,4-difluoro-5-methyl-7-(4-methoxy-2,3,6-trimethylphenyl)-hetatrienoic acid was dissolved in 50 ml. of tetrahydrofuran-ether (2:3) and stirred at −75° C. under argon. A solution of methyl lithium (10 ml., 1.85

M in ether) was then added dropwise in four aliquots of 2.25 ml. each. After the addition was complete, a few drops of water were added to the reaction mixture, which was then poured into ~150 ml. of ice water. Extraction of the resulting aqueous phase with ether and processing the organic phase in the usual manner gave 0.46 g. of a neutral substance containing mainly the 3(Z),5(Z),7(E)-3,5-difluoro-6-methyl-8-(4-methoxy-2,3,6-trimethylphenyl)-octatrien-2-one. The aqueous phase was acidified with concentrated hydrochloric acid and extracted with methylene chloride, which was washed with water, dried over anhydrous magnesium sulfate and concentrated in vacuo to give 2(Z),4(Z),6(E)-2,4-difluoro-5-methyl-7-(4-methoxy-2,3,6-trimethylphenyl)-heptatrienoic acid, mp. 200°–209° C.

The crude 3(Z),5(Z),7(E)-3,5-difluoro-6-methyl-8-(4-methoxy-2,3,6-trimethylphenyl)-octatrien-2-one (3.3 g. from several similar preparations) was purified by chromatography on 250 g. of silica gel. Elution with ether-petroleum ether (1:9) gave yellow crystalline 3(Z),5(Z),7(E)-3,5-difluoro-6-methyl-8-(4-methoxy-2,3,6-trimethylphenyl)-octatrien-2-one as the major product, mp 85°–100° C.

EXAMPLE 50

Ethyl 2(E),4(Z),6(Z),8(E)-3,7-dimethyl-4,6-difluoro-9-(4-methoxy-2,3,6-trimethylphenyl)nonatetraenoate A solution of 2.02 g. (9.02 mmol) of triethyl phosphonoacetate in 7 ml. of dry dimethoxyethane was added dropwise, at ~4° C., under argon, to a stirred suspension of 384 mg. (8.04 mmol) of sodium hydride (50% in oil dispersion, the oil was removed by washing with petroleum ether) in 2 ml. of dry dimethoxyethane. After hydrogen gas ceased to come off, the mixture was stirred at 23° C. under argon for 2.5 hours. A solution of 1.8 g. (5.63 mmol) of 3(Z),5(Z),7(E)-3,5-difluoro-6-methyl-8-(4-methoxy-2,3,6-trimethylphenyl)-octatrien-2-one in 10 ml. of dimethoxyethane was slowly added to the resulting greenish suspension. The resulting reaction mixture was stirred at 23° C. under argon for 18 hours and then poured onto ice-water. The resulting aqueous solution was acidified with 2 N hydrochloric acid and extracted with ether. The ether extracts were combined, washed with water, dried over anhydrous magnesium sulfate and concentrated to give an oily crude product, which was chromatographed on 200 g. of silica gel. Elution with methylene chloride-petroleum ether (2:3) gave a crystalline substance, which on recrystallization from ether-petroleum ether (~1:9) yielded ethyl 2(E),4(Z),6(Z),8(E)-3,7-dimethyl-4,6-difluoro-9-(4-methoxy-2,3,6-trimethylphenyl)-nonatetraenoate as yellow crystals, mp. 110°–118° C.

EXAMPLE 51

Ethyl (E/Z,E)-2-fluoro-6,6-dimethoxy-5-methyl-2,4-hexadienoate

A suspension of 100.84 g. (2.10 mol) of sodium hydride (50% oil dispersion; the oil had been removed by washing with pentane) in 200 ml. of dry dimethoxyethane was stirred at 4° C. under argon, while a solution of 508.62 g. (2.10 mol) of triethyl phosphonofluoroacetate in 500 ml. of dry dimethoxyethane was added dropwise. The mixture was then stirred at 23° C. for 1.5 hours. A solution of 300 g. (2.08 mol) of 4,4-dimethoxy-3-methyl-2-butenal in 500 ml. of dry dimethoxyethane was added dropwise to the resulting orange-brown mixture over a period of 1.0 hour with ice-bath cooling and stirring under argon. The reaction mixture was stirred at 23° C. for 17 hours and then at 60° C. for 3 hours under argon. It was then cooled to ~20° C. and 500 ml. of cold water was slowly added. The resulting solution was further diluted with 1.5 l. of water and worked up with ether in the usual manner to yield a crude product which upon vacuum distillation yielded ethyl (E/Z,E)-2-fluoro-6,6-dimethoxy-5-methyl-2,4-hexadienoate as a colorless liquid, bp 99°–117° C./0.6–0.75 mm.

EXAMPLE 52

Ethyl (E,Z,E)-4-fluoro-3,7-dimethyl-8-oxo-2,4,6-octatrienoate

A solution of 100 g. (0.43 mol) of ethyl (E/Z,E)-2-fluoro-6,6-dimethoxy-5-methyl-2,4-hexadienoate in 1.0 l. of absolute ethanol was stirred with 10.82 g. (0.45 mol) of lithium hydroxide at 23° C. under argon for 20 hours. The residual lithium hydroxide was removed by filtration and washed with 200 ml. of absolute ethanol. Evaporation of the ethanol to dryness at reduced pressure yielded a yellow oil which was further dried at 23° C. over phosphorous pentoxide at 0.5 mm. for 24 hours to yield (E/Z,E)-2-fluoro-6,6-dimethoxy-5-methyl-2,4-hexadienoic acid lithium salt as a yellow semisolid. A sample of 74.76 g. (0.379 mol) of this lithium salt was dissolved in 600 ml. of dry tetrahydrofuran and cooled to −72° C. in a dry ice-acetone bath. A solution of 188.5 ml. (0.379 mol) of methyl lithium (2.01 M in ether) was then added dropwise to the above solution, with stirring at −72° C. under argon. After 15 min. of stirring, another 37.7 ml. (0.076 mol) of methyl lithium was slowly added again. The reaction mixture was stirred at −72° C. under argon for 1.0 hour and then was allowed to warm to 23° C. Water (250 ml.) was slowly added to the reaction mixture and most tetrahydrofuran was removed at reduced pressure. The mixture was worked up with ether in the usual manner to yield (E/Z,E)-3-fluoro-7,7-dimethoxy-6-methyl-3,5-heptadien-2-one as a yellow liquid. This material was used directly for the reaction described below.

A solution of 75.55 g. (0.337 mol) of triethyl phosphonoacetate in 200 ml. of dry dimethoxyethane was added dropwise, with stirring, at 23° C. under argon, to a suspension of 16.17 g. (0.337 mol) of 50% sodium hydride oil dispersion (the oil was removed by washing with pentane) in 25 ml. of dimethoxyethane. After completion of addition the mixture was stirred at 23° C. under argon for 1.0 hour. A solution of 55.71 g. (0.275 mol) of (E/Z,E)-3-fluoro-7,7-dimethoxy-6-methyl-3,5-heptadien-2-one in 200 ml. of dry dimethoxyethane was then added dropwise to the resulting mixture. The reaction mixture was stirred at 23° C. for 2.0 hours and then diluted with ice-water and adjusted to pH 2 with approximately 350 ml. of 1 N hydrochloric acid. It was worked up with ether in the usual manner to yeild a crude product which was filtered through 500 g. of florisil with 1:1 ether-petroleum ether to yield ethyl (E,E/Z,E)-4-fluoro-3,7-dimethyl-8-oxo-2,4,6-octatrienoate. This material was dissolved in 1.5 l. of anhydrous ether and treated with 493 mg. of iodine crystals. The resulting solution was stirred at 23° C. under argon for 24 hours. It was washed with 5% sodium thiosulfate solution, water and dried over anhydrous magnesium sulfate. The ether solution was first concentrated to a small volume at reduced pressure and then passed onto 600 g. of florisil. Elution with ether afforded yellow-orange crystals, which on recrystallization from ether-petroleum ether yielded ethyl (E,Z,E)-4-fluoro-3,7-dimethyl-8-oxo-2,4,6-octatrienoate as orange crystals, mp 70°–74° C.

EXAMPLE 53

Ethyl (E)- and (Z)-2-fluoro-4,4-dimethoxy-3-methyl-2-butenoate

Sodium hydride (64 g. 1.33 mol, 50% dispersion in mineral oil) was suspended in 1500 ml. of dimethylformamide, dried over calcium oxide and distilled at reduced pressure in a 3 l. round-bottom flask fitted with thermometer, mechanical stirrer, argon inlet and dropping funnel. The mixture was cooled to 0° C. and triethylphosphonofluoroacetate (312 g. 1.29 mol) was added slowly over a 30 minute period. Stirring was continued for an additional 0.5 hour and then 195 g. of methylglyoxal dimethylacetal (1.65 mol) was added slowly. The resulting mixture was stirred for 1 hour and then was poured into 3 l. of water and extracted with 1.5 l. of hexane. The hexane was washed twice with 0.5 l. of water and with 0.5 l. of saturated sodium chloride solution. The combined organic extract was dried with sodium sulfate, filtered, and distilled to remove most of the hexane. The product, which was sensitive to strong base, acid, and moisture, was distilled at 65°–68° C. (3 mm.) to give a ~65:35 ratio of ethyl E and Z-2-fluoro-4,4-dimethoxy-3-methyl-2-butenoate.

EXAMPLE 54

Z-2-fluoro-3-methyl-4,4-dimethoxy-2-buten-1-al 15.8 g. (77 mmol) of ethyl Z-2-fluoro-4,4-dimethoxy-3-methyl-2-butenoate was dissolved in 250 ml. of hexane in a 500 ml. round-bottomed flask fitted with a thermometer, argon inlet, and dropping funnel. This was cooled to −75° C. and 63.5 ml. diisobutylaluminum hydride (1.45 equivalent of hydrogen) was added slowly and allowed to stir for 1 hour. Ethyl acetate (8.8 g., 100 mmol) was added and the reaction mixture was allowed to come to −30° C. A mixture of 20 g. of sodium sulfate containing 3.6 g. of water was added and stirring was continued for 1 hour at 25°–35° C. The material was filtered through Celite twice and evaporated on rotary evaporator at 31° C. in glassware which had been rinsed with 8 N ammonium hydroxide and dried. An inert gas atmosphere must be maintained during all work-up operations. The Z-2-fluoro-3-methyl-4,4-dimethoxy-2-buten-1-al obtained was stored at −20° C. under argon and used as quickly as possible in the next step.

EXAMPLE 55

Methyl 2(E,Z),4(E),6(Z)-8,8-dimethoxy-3,7-dimethyl-6-fluoro-2,4,6-octatrienoate

Dimethyl-(2-methyl-3-carbomethoxy-2-propen-1-yl)phosphonate (18.0 g., 81 mmol) was dissolved in 250 ml. of anhydrous tetrahydrofuran in a 500 ml. round-bottomed flask fitted with a thermometer, argon inlet, and septum. The solution was cooled to −60° C. and 36.0 ml. of butyllithium (2.3 M, 83 mmol) was added slowly via syringe. The mixture was stirred for 0.5 hour at −60° C. and then Z-2-fluoro-3-methyl-4,4-dimethoxy-2-buten-1-al was added at −60° C. The reaction was allowed to warm to 0°–5° C. for ½ hour and then was poured into 2 l. of water and extracted with 1.5 l. of hexane. The hexane extract was washed twice with 0.5 l. of water and then with 0.5 l. of saturated sodium chloride solution, dried with 100 g. of sodium sulfate, filtered, and evaporated to give methyl 2(E,Z),4(E),6(Z)-3,7-dimethyl-6-fluoro-8,8-dimethoxy-2,4,6-octatrienoate.

EXAMPLE 56

Methyl 2(E),4(E),6(Z)-3-methyl-6-fluoro-7-formyl-2,4,6-octatrienoate 12.5 g. of methyl 2(E,Z),4(E),6(Z)-3,7-dimethyl-6-fluoro-8,8-dimethoxy-octa-2,4,6-trienoate (12.5 g. 48 mmol) was dissolved in 250 ml. of hexane in an argon atmosphere and 250 ml. of 3 N hydrochloric acid was added with vigorous stirring. After 0.5 hour, 200 ml. of diethyl ether was added to dissolve the solid material. The organic phase was separated and the aqueous layer was extracted with 100 ml. of hexane. The organic extracts were combined and washed with 200 ml. of water and 200 ml. of saturated sodium chloride solution, dried with 50 g. of sodium sulfate, filtered and evaporated. Crystallization at −20° C. from 500 ml. of ether-hexane (1:1) 2(E),4(E),6(Z)-3-methyl-6-fluoro-7-formyl-2,4,6-octatrienoate. The mother liquor was recrystallized from 600 ml. of ether-hexane (1:1.2) at −70° C. to give 2(E,Z),4(E),6(Z)-3-methyl-6-fluoro-7-formyl-2,4,6-octatrienoate, which can be isomerized to give the 2(E),4(E),6(Z)-isomer.

EXAMPLE 57

E-4,4-dimethoxy-2-fluoro-3-methyl-2-buten-1-ol

Ethyl-(E)-2-fluoro-4,4-dimethoxy-3-methyl-2-butenoate (60 g., 0.29 mol) was dissolved in 2500 ml. of pentane in a 5000 ml., round-bottomed flask fitted with argon inlet, thermometer, dropping funnel, and magnetic stirrer and cooled to −70° C. Diisobutylaluminum hydride (496 ml., ~870 mmol, ~3.0 eq.) was added slowly over a 1 hour period. Stirring was continued for 2 hours and then 44 g. (0.5 mol) of ethyl acetate was added and the temperature was allowed to rise to −30° C.

Sodium sulfate (200 g.) containing 54 g. of water was added and the temperature was kept at 30° C. for 2 hours. The resulting material was filtered twice through Celite under argon and evaporated on the rotary evaporator at 31° C. in a flask which had been rinsed with 8 N ammonium hydroxide and dried. An inert gas atmosphere was maintained during all work-up operations. The E-2-fluoro-4,4-dimethoxy-3-methyl-2-buten-1-ol was stored at −20° C. and used in the next step as soon as possible.

EXAMPLE 58

E-4,4-dimethoxy-2-fluoro-3-methyl-buten-1-al

Chromium trioxide (145 g., 1.45 mol) was added to 5 l. of methylene chloride in a 12 l. round bottomed flask fitted with argon inlet and mechanical stirrer. Pyridine (230 ml., 2.9 mol) was added and the mixture was stirred for 2 hours. Celite (290 g.) was added and then E-4,4-dimethoxy-2-fluoro-3-methyl-buten-1-ol was added in one portion and stirred for 30 minutes. The mixture was filtered, evaporated at 30° C. to ~5% of its volume and diluted with 500 ml. of ether. This mixture was filtered and evaporated to ~100 ml. at 30° C. The resulting E-4,4-dimethoxy-2-fluoro-3-methyl-buten-1-al was used in the next step without further purification.

EXAMPLE 59

Methyl-2(E,Z),4(E),6(E),6(E)-8,8-dimethoxy-3,7-dimethyl-6-fluoro-octatrienoate

In a similar manner as described above for the 2(E,Z),4(E),6(Z)-isomer, E-4,4-dimethoxy-2-fluoro-3-methylbuten-1-al was treated at −60° C. with the anion prepared from 65 g. (0.29 mol) of dimethyl-(2-methyl-3-carbomethoxy-2-propen-1-yl) phosphonate and 126 ml. (0.29 mol) of 2.3 M n-butyllithium in 2000 ml. of anhydrous tetrahydrofuran. The reaction mixture was allowed to warm to room temperature for 2 days and then was poured into 3 l. of water and extracted with 1.5 l. of hexane. The organic layer was washed twice with 1 l. of water and then with 0.5 l. of saturated sodium chloride solution, dried with 100 g. of sodium sulfate, filtered, and evaporated. The crude material was filtered through 150 g. of silica gel with 500 ml. of methylene chloride as elutant. Evaporation of the solvent gave methyl 2(E,Z),4(E),6(E)-8,8-dimethoxy-3,7-dimethyl-6-fluoro-octatrienoate.

EXAMPLE 60

Methyl 2(E,Z),4(E),6(E)-3-methyl-6-fluoro-7-formyl-2,4,6-octatrienoate

In a similar manner as described above for the 2(E),4(E),6(Z)-isomer, 31 g. of methyl 2(E,Z),4(E),6(E)-8,8-dimethoxy-3,7-dimethyl-6-fluoro-octatrienoate was dissolved in 250 ml. of hexane and placed in an argon atmosphere. 250 Ml. of 3 N aqueous hydrochloric acid was added with vigorous stirring. After 0.5 hour, the yellow solid which had formed was dissolved in 300 ml. of diethyl ether. The organic layer was separated and the aqueous phase was extracted with 100 ml. of hexane. The combined organic extracts were washed with 200 ml. of water and 200 ml. of saturated aqueous sodium chloride solution, dried with 50 g. of anhydrous sodium sulfate, filtered and evaporated. Crystallization from 500 ml. of ether-hexane (1:2) at −20° C. gave methyl-2(E,Z),4(E),6(E)-3-methyl-6-fluoro-7-formyl-2,4,6-octatrienoate. The mother liquor in 250 ml. of ether at −70° C. yielded additional product.

EXAMPLE 61

Ethyl (E,Z,E,E)-9-(4-methoxy-2,3,6-trimethylphenyl)-4-fluoro-3,7-dimethyl-2,4,6,8-nonatetraenoate A solution of 6.06 ml. (14.4 mmol) of n-butyllithium (2.3 M in hexane) was added dropwise under argon, at −72° C., to a stirred suspension of 4.61 g. (10 mmol) of 4-methoxy-2,3,6-trimethylbenzyl triphenylphosphonium chloride in 25 ml. of dry tetrahydrofuran. After addition of reagent was complete the mixture was stirred at −30° C. until an orange solution was formed. The resulting solution was first cooled to −72° C. and then treated dropwise with a solution of 2.03 g. (9.0 mmol) of ethyl (E,Z,E)-4-fluoro-3,7-dimethyl-8-oxo-2,4,6-octatrienoate in 10 ml. of dry tetrahydrofuran. The reaction mixture was gradually allowed to come to 25° C. and further stirred at this temperature under argon for 2.0 hours. It was poured onto 100 ml. of cold water and extracted with methylene chloride (4×100 ml.). The combined organic extracts were washed with water (2×100 ml.) dried over anhydrous magnesium sulfate and concentrated to give 6.4 g. of oily crude product. This material was filtered through 300 g. of florisil and eluted with methylene chloride to yield 2.97 g. of yellow crystalline substance, which on crystallization from ether-petroleum ether (~1:9) afforded ethyl (E,Z,E,E)-9-(4-methoxy-2,3,6-trimethylphenyl)-4-fluoro-3,7-dimethyl-2,4,6,8-nonatetraenoate as yellow crystals, mp 92°–96° C.

EXAMPLE 62

Methyl (E,E,Z,E)-9-(4-methoxy-2,3,6-trimethylphenyl)-6-fluoro-3,7-dimethyl-2,4,6,8-nonatetraenoate A solution of 20.0 ml. (42.0 mmole) of n-butyllithium (2.1 M in hexane) was added with a syringe, under argon, at −70° C., to a stirred solution of 17.0 g. (38.6 mmole) of 4-methoxy-2,3,6-trimethylbenzyltriphenylphosphonium chloride in 100 ml. of dry tetrahydrofuran. The solution was warmed to −40° c. until a dark solution had formed. This was cooled to −70° C. and 7.5 g. (35.4 mmole) of methyl (E,E,Z)-6-fluoro-3,7-dimethyl-8-oxo-2,4,6-octatrienoate in 25 ml. of dry tetrahydrofuran was added dropwise. The reaction mixture was gradually allowed to come to 25° C. and stirred at this temperature for 1 hour. The material was poured into water, extracted with 1:1 parts by volume hexane-diethyl ether. The combined organic extracts were washed with water, dried over anhydrous magnesium sulfate and concentrated to give an oily crude product. This material was filtered through 300 g. of silica gel and eluted with methylene chloride to yield 12.0 g. of an orange crystalline substance. Crystallization from di-isopropylether gave methyl (E,E,Z,E)-9-(4-methoxy-2,3,6-trimethylphenyl-6-fluoro-3,7-dimethyl-2,4,6,8-nonatetraenoate as orange crystals, m.p. 118°–119° C.

EXAMPLE 63

| Wet Granulation Formulation - 25 mg. Tablets | |
|---|---|
| Ingredients | Per Tablet |
| Active Compound - 2% excess | 25.5 mg. |
| Modified Starch | 2.5 mg. |
| Pregelatinized Starch | 2.5 mg. |
| Microcrystalline Cellulose | 3.5 mg. |
| Lactose, Anhydrous | 3.0 mg. |
| Magnesium Stearate | .3 mg. |
| Talc | .7 mg. |
| Total Weight | 38.0 mg. |

Procedure:
1. Mix all ingredients, except magnesium stearate and talc, in a suitable mixer. Mill and mix.
2. Granulate with water to a uniform wet consistency. Mill and spread on trays.
3. Dry overnight in a suitable dryer.
4. Mill and prepare a premix with magnesium stearate and talc. Mix for 5 minutes.
5. Compress on a suitable press.

EXAMPLE 64

| Direct Compression Formulation - 25 mg. Tablets | |
|---|---|
| Ingredients | Per Tablet |
| Active Compound - 2% excess | 25.5 mg. |
| Lactose, Anhydrous | 172.5 mg. |
| Microcrystalline Cellulose (pH 101) | 25.0 mg. |
| Starch | 25.0 mg. |
| Magnesium Stearate | 2.0 mg. |

| Direct Compression Formulation - 25 mg. Tablets | |
|---|---|
| Ingredients | Per Tablet |
| Total Weight | 250 mg. |

Procedure:

1. Mix all ingredients, except magnesium stearate in a suitable mixer.

| Direct Compression Formulation - 25 mg. Tablets | |
|---|---|
| Ingredients | Per Tablet |

2. Make a premix with magnesium stearate and add to the mix in Step 1. Mix for 5 minutes.
3. Compress on a suitable press.

We claim:
1. Ethyl-7-(4-methoxy-2,3,6-trimethylphenyl)-2-fluoro-5-methyl-2(Z),4(E),6(E)-heptatrienoate.
2. 7-(4-methoxy-2,3,6-trimethylphenyl)-2-fluoro-5-methyl-2(Z),4(E),6(E)-heptatrienoic acid.

* * * * *